United States Patent
Okakura et al.

(10) Patent No.: US 9,512,409 B2
(45) Date of Patent: Dec. 6, 2016

(54) THERMOSTABLE CATALASE

(71) Applicant: MEIJI SEIKA PHARMA CO., LTD., Tokyo (JP)

(72) Inventors: Kaoru Okakura, Odawara (JP); Fusuke Mazuka, Odawara (JP); Takayoshi Fukushima, Odawara (JP); Koichiro Murashima, Odawara (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 14/606,208

(22) Filed: Jan. 27, 2015

(65) Prior Publication Data

US 2015/0132820 A1 May 14, 2015

Related U.S. Application Data

(62) Division of application No. 12/918,017, filed as application No. PCT/JP2009/052729 on Feb. 18, 2009, now Pat. No. 8,975,053.

(30) Foreign Application Priority Data

Feb. 18, 2008 (JP) .................. 2008-036171

(51) Int. Cl.
*C12N 9/08* (2006.01)
*C12N 1/00* (2006.01)
*C12N 15/00* (2006.01)
*C07H 21/04* (2006.01)

(52) U.S. Cl.
CPC ...... *C12N 9/0065* (2013.01); *C12Y 111/01006* (2013.01)

(58) Field of Classification Search
None
See application file for complete search history.

(56) References Cited

U.S. PATENT DOCUMENTS

| | | | |
|---|---|---|---|
| 5,071,439 A | 12/1991 | Weible | |
| 5,571,719 A | 11/1996 | Christensen et al. | |
| 5,646,025 A | 7/1997 | Moyer | |
| 6,159,720 A | 12/2000 | Murashima et al. | |
| 6,277,596 B1 | 8/2001 | Watanabe et al. | |
| 6,337,201 B1 | 1/2002 | Yanai et al. | |
| 6,403,362 B1 | 6/2002 | Moriya et al. | |
| 6,921,655 B1 | 7/2005 | Nakamura et al. | |
| 7,138,263 B2 | 11/2006 | Murashima et al. | |

FOREIGN PATENT DOCUMENTS

| | | |
|---|---|---|
| JP | 49-4956 A | 2/1974 |
| JP | 55-135588 A | 10/1980 |
| JP | 60-083579 A | 5/1985 |
| JP | 63-003788 A | 1/1988 |
| JP | 02-076579 A | 3/1990 |
| JP | 05-153975 A | 6/1993 |
| JP | 06-506347 A | 7/1994 |
| JP | 10179167 | 7/1998 |
| JP | 10-257883 A | 9/1998 |
| JP | 2001-017180 A | 1/2001 |
| JP | 2004-261137 A | 9/2004 |
| JP | 2007-143405 A | 6/2007 |
| WO | 92/17571 A1 | 10/1992 |
| WO | 96/34962 A1 | 11/1996 |
| WO | 97/34004 A1 | 9/1997 |
| WO | 98/03640 A1 | 1/1998 |
| WO | 98/03667 A1 | 1/1998 |
| WO | 98/11239 A1 | 3/1998 |
| WO | 00/24879 A | 5/2000 |
| WO | 00/68401 A1 | 11/2000 |
| WO | 01/90375 A1 | 11/2001 |
| WO | 03070956 | 8/2003 |
| WO | 2008049837 | 5/2008 |

OTHER PUBLICATIONS

Hisada et al. Cloning and Expression Analysis of Two Catalase Genes from Aspergillus oryzae., Journal of Bioscience and Bioengineering, 99: 562-568, 2005.*

Norihiro Tsukagoshi, Kumikae Tanpakushitsu Seisan-hou, "Production of recombinant proteins," Japan Scientific Societies Press, pp. 94-95.

A. V. Kurakov et al., "Search for micromycetes producing extracellular catalase by micromycetes and study conditions of catalase synthesis," Prinkl. Biokhim. Mikrobiol. (ISSN 0555-1099), 2001, pp. 67-72, vol. 37, No. 1.

Extended European Search Report issued May 7, 2012, in corresponding EP Application No. 09711878.0 (in the name of Meiji Seika Kaisha, Ltd.).

A.V. Kurakov et al., "Search for Micromycetes Producing Extracellular Catalase and Study of Conditions of Catalase Synthesis," Applied Biochemistry and Microbiology, 2001, 37(1): 59-64.

Uniprot Accession No. 92405, Feb. 1997, retrieved from http://ibis.internal.epo.org/exam/dbfetch.jsp?id=UNIPROT:Q92405 on Apr. 19, 2012.

Gerben Straatsma et al., "Taxonomy of Seytalidium thermophilum, an important thermophilic fungus in mushroom compost," Mycol. Res., 1993, 97(3): 321-328.

Ramesh Maheshwari et al., "Thermophilic Fungi: Their Physiology and Enzymes," Microbiology and Molecular Biology Reviews, 2000, 64(3): 461-488.

EBI Accession No. EM_FUN: U97574, Oct. 1997, retrieved from http://ibis.internal.epo.org/exam/dbfetch.jsp?id=EM_FUN:U97574.

Whisstock et al., "Prediction of protein function from protein sequence and structure," Quarterly Reviews of Biophysics, 2003, 36(3): 307-340.

Witkowski et al., "Conversion of a beta-ketoacyl synthase to a malonyl decarboxylase by replacement of the active-site cysteine with glutamine," Biochemistry. Sep. 7, 1999; 38(36): 11643-50.

* cited by examiner

*Primary Examiner* — Iqbal H Chowdhury

(74) *Attorney, Agent, or Firm* — Sughrue Mion, PLLC

(57) ABSTRACT

An object is to efficiently produce thermostable catalase at low cost by expressing it as a recombinant protein in large quantity. A recombinant microorganism capable of efficiently expressing thermostable catalase can be provided by obtaining a DNA necessary for efficiently producing it as a recombinant protein, and the thermostable catalase can be efficiently produced at low cost by cultivating the obtained recombinant microorganism. Hydrogen peroxide can be efficiently decomposed at low cost, even at high temperature, by treating a solution containing hydrogen peroxide with the thermostable catalase of the present invention.

20 Claims, 2 Drawing Sheets

SEQUENCE LISTING

```
<160> NUMBER OF SEQ ID NOS: 24

<210> SEQ ID NO 1
<211> LENGTH: 2403
<212> TYPE: DNA
<213> ORGANISM: Penicillium pinophilum
<220> FEATURE:
<221> NAME/KEY: sig_peptide
<222> LOCATION: (1)..(126)
<220> FEATURE:
<221> NAME/KEY: exon
<222> LOCATION: (1)..(321)
<220> FEATURE:
<221> NAME/KEY: CDS
<222> LOCATION: (1)..(321)
<220> FEATURE:
<221> NAME/KEY: mat_peptide
<222> LOCATION: (127)..(2400)
<220> FEATURE:
<221> NAME/KEY: Intron
<222> LOCATION: (322)..(372)
<220> FEATURE:
<221> NAME/KEY: exon
<222> LOCATION: (373)..(598)
<220> FEATURE:
<221> NAME/KEY: CDS
<222> LOCATION: (373)..(598)
<220> FEATURE:
<221> NAME/KEY: Intron
<222> LOCATION: (599)..(651)
<220> FEATURE:
<221> NAME/KEY: exon
<222> LOCATION: (652)..(1067)
<220> FEATURE:
<221> NAME/KEY: CDS
<222> LOCATION: (652)..(1067)
```

```
<220> FEATURE:
<221> NAME/KEY: Intron
<222> LOCATION: (1068)..(1113)
<220> FEATURE:
<221> NAME/KEY: exon
<222> LOCATION: (1114)..(1278)
<220> FEATURE:
<221> NAME/KEY: CDS
<222> LOCATION: (1114)..(1278)
<220> FEATURE:
<221> NAME/KEY: Intron
<222> LOCATION: (1279)..(1326)
<220> FEATURE:
<221> NAME/KEY: exon
<222> LOCATION: (1327)..(2400)
<220> FEATURE:
<221> NAME/KEY: CDS
<222> LOCATION: (1327)..(2400)

<400> SEQUENCE: 1 atg cga gga tta tac tcc ctc ggc gcc ttc gcc agt ctc att gcg gcg      48
Met Arg Gly Leu Tyr Ser Leu Gly Ala Phe Ala Ser Leu Ile Ala Ala
        -40                 -35                 -30 gct tcg gct gca tgc cca atg ctg act ggc gaa atc cca gct ggt agt      96
Ala Ser Ala Ala Cys Pro Met Leu Thr Gly Glu Ile Pro Ala Gly Ser
    -25                 -20                 -15 gtt gcc aat cct cat cat cac gga aag cgt gac gat tca aat gct tcc     144
Val Ala Asn Pro His His His Gly Lys Arg Asp Asp Ser Asn Ala Ser
-10                  -5                  -1  1                 5 tcc gaa aca gaa gcc ttt ctg tcc gag ttc tac ctc aac gac aac gat     192
Ser Glu Thr Glu Ala Phe Leu Ser Glu Phe Tyr Leu Asn Asp Asn Asp
                10                  15                  20 gcc tat ctc acc acc gat gta ggc ggt ccg atc gag gat caa aac agt     240
Ala Tyr Leu Thr Thr Asp Val Gly Gly Pro Ile Glu Asp Gln Asn Ser
        25                  30                  35 ttg aag gcc ggc att cgt gga tcg acc ctc ttg gaa gac ttc atc ttc     288
Leu Lys Ala Gly Ile Arg Gly Ser Thr Leu Leu Glu Asp Phe Ile Phe
    40                  45                  50 cgt cag aaa atc cag cat ttt gat cat gag cgt gtaggttatc cattctatca   341
Arg Gln Lys Ile Gln His Phe Asp His Glu Arg
55                  60                  65 cgtacttcag gggtagttct gacatgccca g gtc ccg gaa cgt gcc gtg cat      393
                                  Val Pro Glu Arg Ala Val His
                                                          70 gct cga ggt gca ggt gct cat ggt gta ttt act tca tat gcc gac tgg     441
Ala Arg Gly Ala Gly Ala His Gly Val Phe Thr Ser Tyr Ala Asp Trp
        75                  80                  85 tcc aac atc act gct gct tca ttt ttg gga gct tcc gga aag gaa acg     489
Ser Asn Ile Thr Ala Ala Ser Phe Leu Gly Ala Ser Gly Lys Glu Thr
    90                  95                  100 ccc aca ttt gtc cgc ttc tcg act gtt gca ggc agc cga gga agt gcc     537
Pro Thr Phe Val Arg Phe Ser Thr Val Ala Gly Ser Arg Gly Ser Ala
105                 110                 115                 120 gac acc gct cgt gac gtt cac gga ttt gct act cgc ttc tat act gac     585
Asp Thr Ala Arg Asp Val His Gly Phe Ala Thr Arg Phe Tyr Thr Asp
            125                 130                 135 gag gga aac tat g gtagcctttc tctttgactc gtccatagat agggatgtaa       638
Glu Gly Asn Tyr
            140 ctgacttcaa cag ac att gtt gga aac aac att cct gtc ttc ttc atc       686
              Asp Ile Val Gly Asn Asn Ile Pro Val Phe Phe Ile
                                145                 150
```

| | | |
|---|---|---|
| caa gat gct atc tta ttc cca gat ctc atc cat agc gtt aag cca cag | | 734 |
| Gln Asp Ala Ile Leu Phe Pro Asp Leu Ile His Ser Val Lys Pro Gln | | |
| 155 160 165 | | |
| cca gcc aat gaa atc cca cag gct gct act gca cac gac acg gcc tat | | 782 |
| Pro Ala Asn Glu Ile Pro Gln Ala Ala Thr Ala His Asp Thr Ala Tyr | | |
| 170 175 180 | | |
| gac ttc ttt ggt caa cag cca agc act ctg cat acc ctc ttc tgg gca | | 830 |
| Asp Phe Phe Gly Gln Gln Pro Ser Thr Leu His Thr Leu Phe Trp Ala | | |
| 185 190 195 200 | | |
| atg gca ggc cat ggt atc cca cgg tct ttc cgt cat gtt gac gga ttc | | 878 |
| Met Ala Gly His Gly Ile Pro Arg Ser Phe Arg His Val Asp Gly Phe | | |
| 205 210 215 | | |
| ggt gtc cac acc tat cgg ttc gtg aca gat gat ggc tcg tcc aag ttg | | 926 |
| Gly Val His Thr Tyr Arg Phe Val Thr Asp Asp Gly Ser Ser Lys Leu | | |
| 220 225 230 | | |
| gtc aaa ttt cac tgg aca tcg ctg caa ggt cgg gcc agt ctg gtc tgg | | 974 |
| Val Lys Phe His Trp Thr Ser Leu Gln Gly Arg Ala Ser Leu Val Trp | | |
| 235 240 245 | | |
| gag gaa gct cag gcc act gct ggc aaa aat gcc gac ttt atg aga cag | | 1022 |
| Glu Glu Ala Gln Ala Thr Ala Gly Lys Asn Ala Asp Phe Met Arg Gln | | |
| 250 255 260 | | |
| gat ctg tat gat agc att gag gct ggc cgt tat cca gag tgg gag | | 1067 |
| Asp Leu Tyr Asp Ser Ile Glu Ala Gly Arg Tyr Pro Glu Trp Glu | | |
| 265 270 275 | | |
| gtatgtacca ccgaattcat ggaaagtact cgactaacgt gaacag ctc ggc gtg | | 1122 |
| Leu Gly Val | | |
| 280 | | |
| caa ata att gag gag tcg gat gtc tta agc tac gga ttt gac ctg ttg | | 1170 |
| Gln Ile Ile Glu Glu Ser Asp Val Leu Ser Tyr Gly Phe Asp Leu Leu | | |
| 285 290 295 | | |
| gat cca acc aag att ctt ccg gtt gaa aaa gtt cca att act gcg ctc | | 1218 |
| Asp Pro Thr Lys Ile Leu Pro Val Glu Lys Val Pro Ile Thr Ala Leu | | |
| 300 305 310 | | |
| gga aaa atg caa ctc aac cgt aat cca ttg aat tac ttt gcc gag aca | | 1266 |
| Gly Lys Met Gln Leu Asn Arg Asn Pro Leu Asn Tyr Phe Ala Glu Thr | | |
| 315 320 325 330 | | |
| gag caa gtc atg gtaagtcgac cttccggcac tcgagtcatt tcctactaac | | 1318 |
| Glu Gln Val Met | | |
| gtggatag ttc caa cct ggc cac att gtt cgt ggt atc gac ttc acc tat | | 1368 |
| Phe Gln Pro Gly His Ile Val Arg Gly Ile Asp Phe Thr Tyr | | |
| 335 340 345 | | |
| tat cct ctt ctc cag ggt cgt tta ttc tcc tac ctc gat act cag ctg | | 1416 |
| Tyr Pro Leu Leu Gln Gly Arg Leu Phe Ser Tyr Leu Asp Thr Gln Leu | | |
| 350 355 360 | | |
| aat cgc aat ggt ggt ccc aac ttt gaa caa att cca atc aat cgt ccg | | 1464 |
| Asn Arg Asn Gly Gly Pro Asn Phe Glu Gln Ile Pro Ile Asn Arg Pro | | |
| 365 370 375 380 | | |
| cgt gtt cct atc cac aac aac aac cgc gat gga ttc gcc caa atg ttt | | 1512 |
| Arg Val Pro Ile His Asn Asn Asn Arg Asp Gly Phe Ala Gln Met Phe | | |
| 385 390 395 | | |
| att cct ttg aac cag gca gca tat tca ccc aac acc ttg aat aat ggc | | 1560 |
| Ile Pro Leu Asn Gln Ala Ala Tyr Ser Pro Asn Thr Leu Asn Asn Gly | | |
| 400 405 410 | | |
| tct cct cga caa gcc aac gag act gtc gga aat ggc ttc ttt acc gcc | | 1608 |
| Ser Pro Arg Gln Ala Asn Glu Thr Val Gly Asn Gly Phe Phe Thr Ala | | |
| 415 420 425 | | |
| ccc ggg cgc tcc gca gat gga cac ctt gtt cgc gct acg agc cca aca | | 1656 |
| Pro Gly Arg Ser Ala Asp Gly His Leu Val Arg Ala Thr Ser Pro Thr | | |
| 430 435 440 | | |

```
ttt gcc gac gtg tgg tct cag cct ggc ttg ttt tac aac tcc ttg acg      1704
Phe Ala Asp Val Trp Ser Gln Pro Gly Leu Phe Tyr Asn Ser Leu Thr
445                 450                 455                 460 gct acc gaa caa cag ttc gtg atc aat gct ttg cgt ttc gaa ttg tct      1752
Ala Thr Glu Gln Gln Phe Val Ile Asn Ala Leu Arg Phe Glu Leu Ser
            465                 470                 475 aat gta aag agc gag gat gtt aaa agc aat ttc atc aca cag ata aat      1800
Asn Val Lys Ser Glu Asp Val Lys Ser Asn Phe Ile Thr Gln Ile Asn
        480                 485                 490 cgc gta aac aac acg tta gca aca ctt gtg gct tct gca att gga gtc      1848
Arg Val Asn Asn Thr Leu Ala Thr Leu Val Ala Ser Ala Ile Gly Val
    495                 500                 505 tcc gcg ccc gaa ccc gac tct aca tac tac cac agc aat aag acg tct      1896
Ser Ala Pro Glu Pro Asp Ser Thr Tyr Tyr His Ser Asn Lys Thr Ser
510                 515                 520 aat gtc gga aca ttc ggt act ccg ttg aaa aag ctt gac ggt ctc aag      1944
Asn Val Gly Thr Phe Gly Thr Pro Leu Lys Lys Leu Asp Gly Leu Lys
525                 530                 535                 540 gtc gga gtc ctt gct tcg gtg aac ggt gaa agt agt att gcc gag gga      1992
Val Gly Val Leu Ala Ser Val Asn Gly Glu Ser Ser Ile Ala Glu Gly
            545                 550                 555 caa gca ttg gca caa agc cta gcg ggc tcg aac gtg gac gtc gtt atc      2040
Gln Ala Leu Ala Gln Ser Leu Ala Gly Ser Asn Val Asp Val Val Ile
        560                 565                 570 gtc gcc gag cat ctt act tcg aac gtg tca gct aca tac tct gga tca      2088
Val Ala Glu His Leu Thr Ser Asn Val Ser Ala Thr Tyr Ser Gly Ser
    575                 580                 585 gac gca acg aac ttt gat gct gtt att gtc agc tca ggg gct gaa ggt      2136
Asp Ala Thr Asn Phe Asp Ala Val Ile Val Ser Ser Gly Ala Glu Gly
590                 595                 600 ctc ttt gga cct caa acc ttt aca gcc gaa tcc aat aca aca ctt tat      2184
Leu Phe Gly Pro Gln Thr Phe Thr Ala Glu Ser Asn Thr Thr Leu Tyr
605                 610                 615                 620 ccg gca ggc cgt cct agc cag att ttg gtc gat gcc ttc cgc ttt ggc      2232
Pro Ala Gly Arg Pro Ser Gln Ile Leu Val Asp Ala Phe Arg Phe Gly
            625                 630                 635 aag ccg gtt gga gca gtt ggt ggt gcc agt gca gct ctg tca gcg gtg      2280
Lys Pro Val Gly Ala Val Gly Gly Ala Ser Ala Ala Leu Ser Ala Val
        640                 645                 650 gat atc agt act gat cgt agt ggt gtg att act ggt gat tcc gtc agt      2328
Asp Ile Ser Thr Asp Arg Ser Gly Val Ile Thr Gly Asp Ser Val Ser
    655                 660                 665 gac gac ttt gtc aag cag cta acg gag gac ctt gcc aca ttc aaa ttc      2376
Asp Asp Phe Val Lys Gln Leu Thr Glu Asp Leu Ala Thr Phe Lys Phe
670                 675                 680 ttg gac cga ttc gct gtg gat gag tag                                  2403
Leu Asp Arg Phe Ala Val Asp Glu
685                 690

<210> SEQ ID NO 2
<211> LENGTH: 734
<212> TYPE: PRT
<213> ORGANISM: Penicillium pinophilum

<400> SEQUENCE: 2

Met Arg Gly Leu Tyr Ser Leu Gly Ala Phe Ala Ser Leu Ile Ala Ala
            -40                 -35                 -30

Ala Ser Ala Ala Cys Pro Met Leu Thr Gly Glu Ile Pro Ala Gly Ser
        -25                 -20                 -15

Val Ala Asn Pro His His His Gly Lys Arg Asp Asp Ser Asn Ala Ser
```

```
        -10              -5              -1 1              5
Ser Glu Thr Glu Ala Phe Leu Ser Glu Phe Tyr Leu Asn Asp Asn Asp
                10              15              20

Ala Tyr Leu Thr Thr Asp Val Gly Gly Pro Ile Glu Asp Gln Asn Ser
                25              30              35

Leu Lys Ala Gly Ile Arg Gly Ser Thr Leu Leu Glu Asp Phe Ile Phe
                40              45              50

Arg Gln Lys Ile Gln His Phe Asp His Glu Arg Val Pro Glu Arg Ala
55              60              65              70

Val His Ala Arg Gly Ala Gly Ala His Gly Val Phe Thr Ser Tyr Ala
                75              80              85

Asp Trp Ser Asn Ile Thr Ala Ala Ser Phe Leu Gly Ala Ser Gly Lys
                90              95              100

Glu Thr Pro Thr Phe Val Arg Phe Ser Thr Val Ala Gly Ser Arg Gly
                105             110             115

Ser Ala Asp Thr Ala Arg Asp Val His Gly Phe Ala Thr Arg Phe Tyr
                120             125             130

Thr Asp Glu Gly Asn Tyr Asp Ile Val Gly Asn Asn Ile Pro Val Phe
135             140             145             150

Phe Ile Gln Asp Ala Ile Leu Phe Pro Asp Leu Ile His Ser Val Lys
                155             160             165

Pro Gln Pro Ala Asn Glu Ile Pro Gln Ala Thr Ala His Asp Thr
                170             175             180

Ala Tyr Asp Phe Phe Gly Gln Gln Pro Ser Thr Leu His Thr Leu Phe
                185             190             195

Trp Ala Met Ala Gly His Gly Ile Pro Arg Ser Phe Arg His Val Asp
                200             205             210

Gly Phe Gly Val His Thr Tyr Arg Phe Val Thr Asp Asp Gly Ser Ser
215             220             225             230

Lys Leu Val Lys Phe His Trp Thr Ser Leu Gln Gly Arg Ala Ser Leu
                235             240             245

Val Trp Glu Glu Ala Gln Ala Thr Ala Gly Lys Asn Ala Asp Phe Met
                250             255             260

Arg Gln Asp Leu Tyr Asp Ser Ile Glu Ala Gly Arg Tyr Pro Glu Trp
                265             270             275

Glu Leu Gly Val Gln Ile Ile Glu Glu Ser Asp Val Leu Ser Tyr Gly
                280             285             290

Phe Asp Leu Leu Asp Pro Thr Lys Ile Leu Pro Val Glu Lys Val Pro
295             300             305             310

Ile Thr Ala Leu Gly Lys Met Gln Leu Asn Arg Asn Pro Leu Asn Tyr
                315             320             325

Phe Ala Glu Thr Glu Gln Val Met Phe Gln Pro Gly His Ile Val Arg
                330             335             340

Gly Ile Asp Phe Thr Tyr Tyr Pro Leu Leu Gln Gly Arg Leu Phe Ser
                345             350             355

Tyr Leu Asp Thr Gln Leu Asn Arg Asn Gly Gly Pro Asn Phe Glu Gln
                360             365             370

Ile Pro Ile Asn Arg Pro Arg Val Pro Ile His Asn Asn Asn Arg Asp
375             380             385             390

Gly Phe Ala Gln Met Phe Ile Pro Leu Asn Gln Ala Ala Tyr Ser Pro
                395             400             405

Asn Thr Leu Asn Asn Gly Ser Pro Arg Gln Ala Asn Glu Thr Val Gly
                410             415             420
```

```
Asn Gly Phe Phe Thr Ala Pro Gly Arg Ser Ala Asp Gly His Leu Val
        425                 430                 435

Arg Ala Thr Ser Pro Thr Phe Ala Asp Val Trp Ser Gln Pro Gly Leu
        440                 445                 450

Phe Tyr Asn Ser Leu Thr Ala Thr Glu Gln Gln Phe Val Ile Asn Ala
455                 460                 465                 470

Leu Arg Phe Glu Leu Ser Asn Val Lys Ser Glu Asp Val Lys Ser Asn
                475                 480                 485

Phe Ile Thr Gln Ile Asn Arg Val Asn Asn Thr Leu Ala Thr Leu Val
                490                 495                 500

Ala Ser Ala Ile Gly Val Ser Ala Pro Glu Pro Asp Ser Thr Tyr Tyr
        505                 510                 515

His Ser Asn Lys Thr Ser Asn Val Gly Thr Phe Gly Thr Pro Leu Lys
        520                 525                 530

Lys Leu Asp Gly Leu Lys Val Gly Val Leu Ala Ser Val Asn Gly Glu
535                 540                 545                 550

Ser Ser Ile Ala Glu Gly Gln Ala Leu Ala Gln Ser Leu Ala Gly Ser
                555                 560                 565

Asn Val Asp Val Val Ile Val Ala Glu His Leu Thr Ser Asn Val Ser
        570                 575                 580

Ala Thr Tyr Ser Gly Ser Asp Ala Thr Asn Phe Asp Ala Val Ile Val
        585                 590                 595

Ser Ser Gly Ala Glu Gly Leu Phe Gly Pro Gln Thr Phe Thr Ala Glu
        600                 605                 610

Ser Asn Thr Thr Leu Tyr Pro Ala Gly Arg Pro Ser Gln Ile Leu Val
615                 620                 625                 630

Asp Ala Phe Arg Phe Gly Lys Pro Val Gly Ala Val Gly Gly Ala Ser
                635                 640                 645

Ala Ala Leu Ser Ala Val Asp Ile Ser Thr Asp Arg Ser Gly Val Ile
        650                 655                 660

Thr Gly Asp Ser Val Ser Asp Phe Val Lys Gln Leu Thr Glu Asp
        665                 670                 675

Leu Ala Thr Phe Lys Phe Leu Asp Arg Phe Ala Val Asp Glu
        680                 685                 690

<210> SEQ ID NO 3
<211> LENGTH: 2749
<212> TYPE: DNA
<213> ORGANISM: Humicola grisea
<220> FEATURE:
<221> NAME/KEY: sig_peptide
<222> LOCATION: (1)..(96)
<220> FEATURE:
<221> NAME/KEY: exon
<222> LOCATION: (1)..(282)
<220> FEATURE:
<221> NAME/KEY: CDS
<222> LOCATION: (1)..(282)
<220> FEATURE:
<221> NAME/KEY: mat_peptide
<222> LOCATION: (97)..(2746)
<220> FEATURE:
<221> NAME/KEY: Intron
<222> LOCATION: (283)..(463)
<220> FEATURE:
<221> NAME/KEY: exon
<222> LOCATION: (464)..(666)
<220> FEATURE:
<221> NAME/KEY: CDS
<222> LOCATION: (464)..(666)
<220> FEATURE:
```

<220> FEATURE:
<221> NAME/KEY: Intron
<222> LOCATION: (667)..(747)
<220> FEATURE:
<221> NAME/KEY: exon
<222> LOCATION: (748)..(770)
<220> FEATURE:
<221> NAME/KEY: CDS
<222> LOCATION: (748)..(770)
<220> FEATURE:
<221> NAME/KEY: Intron
<222> LOCATION: (771)..(846)
<220> FEATURE:
<221> NAME/KEY: exon
<222> LOCATION: (847)..(1007)
<220> FEATURE:
<221> NAME/KEY: CDS
<222> LOCATION: (847)..(1007)
<220> FEATURE:
<221> NAME/KEY: Intron
<222> LOCATION: (1008)..(1160)
<220> FEATURE:
<221> NAME/KEY: exon
<222> LOCATION: (1161)..(1217)
<220> FEATURE:
<221> NAME/KEY: CDS
<222> LOCATION: (1161)..(1217)
<220> FEATURE:
<221> NAME/KEY: Intron
<222> LOCATION: (1218)..(1270)
<220> FEATURE:
<221> NAME/KEY: exon
<222> LOCATION: (1271)..(1841)
<220> FEATURE:
<221> NAME/KEY: CDS
<222> LOCATION: (1271)..(1841)
<220> FEATURE:
<221> NAME/KEY: Intron
<222> LOCATION: (1842)..(1895)
<220> FEATURE:
<221> NAME/KEY: exon
<222> LOCATION: (1896)..(2746)
<220> FEATURE:
<221> NAME/KEY: CDS
<222> LOCATION: (1896)..(2746)

<400> SEQUENCE: 3

```
atg aac aga gtc acg aat ctc ctc gcc tgg gcc ggc gcg ata ggg ctc      48
Met Asn Arg Val Thr Asn Leu Leu Ala Trp Ala Gly Ala Ile Gly Leu
    -30                 -25                 -20 gcc caa gca aca tgc ccc ttc gcg gac cct gcc gct ctg tat agg cgt      96
Ala Gln Ala Thr Cys Pro Phe Ala Asp Pro Ala Ala Leu Tyr Arg Arg
-15                 -10                  -5                  -1 cag gat act acc agc ggc cag tcg cca ctt gca gca tac gag gtg gat     144
Gln Asp Thr Thr Ser Gly Gln Ser Pro Leu Ala Ala Tyr Glu Val Asp
1                   5                  10                  15 gac agc acc gga tac ctg acc tcc gat gtt ggc ggg ccc att cag gac     192
Asp Ser Thr Gly Tyr Leu Thr Ser Asp Val Gly Gly Pro Ile Gln Asp
                20                  25                  30 cag acc agc ctc aag gca ggc atc cgg ggt ccg acc ctt ctt gag gac     240
Gln Thr Ser Leu Lys Ala Gly Ile Arg Gly Pro Thr Leu Leu Glu Asp
            35                  40                  45 ttt atg ttc cgc cag aag atc cag cac ttc gac cat gaa cgg             282
Phe Met Phe Arg Gln Lys Ile Gln His Phe Asp His Glu Arg
        50                  55                  60 gtaaggacat aatgctcaca cgagcggctg cgtacctatt tattttgaac gggtaaggac   342
ataatgctca cacgagcggc tgcgtaccta tttatttccg agagatgggc tggctggctg   402
gctgtgatgc ctgagtttgg ggacatacgg agtaccttac tgacgcgcta atccactcca   462 g gtt ccc gaa agg gcg gtc cat gct cga ggc gct gga gca cac ggg acc   511
  Val Pro Glu Arg Ala Val His Ala Arg Gly Ala Gly Ala His Gly Thr
```

```
                     65                  70                  75
ttc acg agt tac gcc gac tgg agt aac atc acc gcg gcg tcc ttt ctg      559
Phe Thr Ser Tyr Ala Asp Trp Ser Asn Ile Thr Ala Ala Ser Phe Leu
     80                  85                  90 aac gcc aca gga aag cag acg ccg gtg ttt gtc cgg ttc tcg acc gtt      607
Asn Ala Thr Gly Lys Gln Thr Pro Val Phe Val Arg Phe Ser Thr Val
 95                 100                 105                 110 gct ggg tct cga ggg agc gca gac acg gcg aga gac gtt cat ggt ttc      655
Ala Gly Ser Arg Gly Ser Ala Asp Thr Ala Arg Asp Val His Gly Phe
                115                 120                 125 gcg acg cgg tt  gtaagttttg ttgtgtttca ttcgttccgg tctgtagagg          706
Ala Thr Arg Phe
        130 agggttagga tatgagctaa cgtgtgtgtg tgtgtgtgaa g t tac act gat gaa      760
                                              Tyr Thr Asp Glu ggc aac ttt g gtacgtccca cgcatggtcc tcaattctct tatctggcag            810
Gly Asn Phe
135 cgatgtggtc attgtcgacg ttgctaactt gcgtag at  atc gtc gga aac aac      863
                                           Asp Ile Val Gly Asn Asn
                                                           140 atc ccg gta ttc ttc att caa gat gca atc cag ttc cct gac ctt atc      911
Ile Pro Val Phe Phe Ile Gln Asp Ala Ile Gln Phe Pro Asp Leu Ile
145                 150                 155 cac tcg gtc aag ccg agt cca gac aac gag att ccc caa gcg gcg acg      959
His Ser Val Lys Pro Ser Pro Asp Asn Glu Ile Pro Gln Ala Ala Thr
160                 165                 170                 175 gct cat gat tca gct tgg gac ttc ttc agc cag cag cca agc gcc atg     1007
Ala His Asp Ser Ala Trp Asp Phe Phe Ser Gln Gln Pro Ser Ala Met
                180                 185                 190 gtaagcaatg gaccaaggag ccgcacctgg ggtgacatac cagggagtac acggggcgtt   1067
ccgatgaccc tcgtgtgacc aaggcagtac aacactccac ggaggactcg aagagattcg   1127
gaaatatgga acacagaact gacaggatgg tag cac acg ttg ttc tgg gcc atg    1181
                                     His Thr Leu Phe Trp Ala Met
                                                         195 tct ggc cac gga atc cct cgc agc tat cgc cat atg gtacgtttgc          1227
Ser Gly His Gly Ile Pro Arg Ser Tyr Arg His Met
    200                 205                 210 ctggctgaga tgaccgtgaa tccatttcta acctcaagtc cag gat ggc ttc ggc     1282
                                                Asp Gly Phe Gly gtc cac acg ttc cgg ttt gtc aaa gat gac ggc tcg tcc aag ttg atc     1330
Val His Thr Phe Arg Phe Val Lys Asp Asp Gly Ser Ser Lys Leu Ile
215                 220                 225                 230 aag tgg cat ttc aag tca cgc cag gga aag gcg agt cta gtc tgg gaa     1378
Lys Trp His Phe Lys Ser Arg Gln Gly Lys Ala Ser Leu Val Trp Glu
                235                 240                 245 gag gcg cag gtt ctt tct ggc aag aat gcc gac ttc cac cgt cag gac     1426
Glu Ala Gln Val Leu Ser Gly Lys Asn Ala Asp Phe His Arg Gln Asp
            250                 255                 260 ctc tgg gat gct att gag tcc ggg aac gga cca gaa tgg gat gtc tgc     1474
Leu Trp Asp Ala Ile Glu Ser Gly Asn Gly Pro Glu Trp Asp Val Cys
        265                 270                 275 gtc cag att gtc gat gag tcc cag gcg caa gcc ttt ggc ttc gac ttg     1522
Val Gln Ile Val Asp Glu Ser Gln Ala Gln Ala Phe Gly Phe Asp Leu
    280                 285                 290 ctg gac ccg aca aag atc atc ccc gag gag tac gcc ccc ttg acg aaa     1570
Leu Asp Pro Thr Lys Ile Ile Pro Glu Glu Tyr Ala Pro Leu Thr Lys
295                 300                 305                 310
```

```
ctg ggg ctc ttg aag ctg gat cgc aat ccg acc aac tac ttc gcc gag    1618
Leu Gly Leu Leu Lys Leu Asp Arg Asn Pro Thr Asn Tyr Phe Ala Glu
            315                 320                 325 acg gag cag gtc atg ttc caa ccc ggt cat ata gtc cgc ggc gtc gac    1666
Thr Glu Gln Val Met Phe Gln Pro Gly His Ile Val Arg Gly Val Asp
            330                 335                 340 ttc acg gag gat ccc ctg cta cag gga cgt ctc ttc tcg tac ctt gac    1714
Phe Thr Glu Asp Pro Leu Leu Gln Gly Arg Leu Phe Ser Tyr Leu Asp
            345                 350                 355 acg cag ctg aac cgg aat ggc ggg ccc aac ttt gag cag ctg ccc atc    1762
Thr Gln Leu Asn Arg Asn Gly Gly Pro Asn Phe Glu Gln Leu Pro Ile
            360                 365                 370 aac atg ccg cgg gtg ccg att cac aac aat aat cgc gac ggc gcc ggc    1810
Asn Met Pro Arg Val Pro Ile His Asn Asn Asn Arg Asp Gly Ala Gly
375                 380                 385                 390 cag atg ttc atc cac agg aac aag tat cct t gtaagtacct cttttgcctc    1861
Gln Met Phe Ile His Arg Asn Lys Tyr Pro
            395                 400 gatcgttgtg gtgccggctt gctgacagac gcag ac  act ccc aac acc ctg aac  1915
                                         Tyr Thr Pro Asn Thr Leu Asn
                                                             405 agt ggt tat ccg cgg caa gcc aac caa aat gcc gga cgc gga ttc ttc    1963
Ser Gly Tyr Pro Arg Gln Ala Asn Gln Asn Ala Gly Arg Gly Phe Phe
            410                 415                 420 aca gcg cct ggc cgt acc gtc agc ggt gcc ctc gtc cgt gag gtg tcg    2011
Thr Ala Pro Gly Arg Thr Val Ser Gly Ala Leu Val Arg Glu Val Ser
            425                 430                 435 cca aca ttc aac gac cac tgg tcg cag ccc cgt ctc ttc ttc aac tcc    2059
Pro Thr Phe Asn Asp His Trp Ser Gln Pro Arg Leu Phe Phe Asn Ser
440                 445                 450                 455 ctc act ccc gtc gaa cag cag ttc ctc gtc aac gcc atg cgc ttc gaa    2107
Leu Thr Pro Val Glu Gln Gln Phe Leu Val Asn Ala Met Arg Phe Glu
            460                 465                 470 atc agc ctt gtg aag tcg gaa gaa tgc agg aag aac gtg ctc acc cag    2155
Ile Ser Leu Val Lys Ser Glu Glu Cys Arg Lys Asn Val Leu Thr Gln
            475                 480                 485 ctc aac cgc gtc agc cat gat gtg gcc gtg cgc gtg gcc gcc gct atc    2203
Leu Asn Arg Val Ser His Asp Val Ala Val Arg Val Ala Ala Ala Ile
            490                 495                 500 ggc ctc gcc gcg ccc gac gcg gac gac aca tac tac cac aac aac aag    2251
Gly Leu Ala Ala Pro Asp Ala Asp Asp Thr Tyr Tyr His Asn Asn Lys
            505                 510                 515 acg gct ggc gtc tcg atc ctt gga agc ggg ccc ttg cct acc atc aag    2299
Thr Ala Gly Val Ser Ile Leu Gly Ser Gly Pro Leu Pro Thr Ile Lys
520                 525                 530                 535 act ctc cgc gtc ggc atc ctg gct acc acg agc gag tcg agc gcg ctg    2347
Thr Leu Arg Val Gly Ile Leu Ala Thr Thr Ser Glu Ser Ser Ala Leu
            540                 545                 550 gat cag gca gcc cag ctc cgc acc cgt ctg gaa aag gac ggg ctt gtg    2395
Asp Gln Ala Ala Gln Leu Arg Thr Arg Leu Glu Lys Asp Gly Leu Val
            555                 560                 565 gtc acg gtt gtg gct gaa acg ctg cgc gag ggg gta gac cag aca tac    2443
Val Thr Val Val Ala Glu Thr Leu Arg Glu Gly Val Asp Gln Thr Tyr
            570                 575                 580 tcg acg gcg gat gcc acg ggt ttc gac ggc gtt gtt gtt gtg gac ggg    2491
Ser Thr Ala Asp Ala Thr Gly Phe Asp Gly Val Val Val Val Asp Gly
585                 590                 595 gcg gcg gcg ctg ttt gcc agc acc gcg tcg tcg ccg ttg ttc ccg acg    2539
Ala Ala Ala Leu Phe Ala Ser Thr Ala Ser Ser Pro Leu Phe Pro Thr
```

```
                600             605             610             615
ggc agg ccg ttg cag atc ttt gtg gac gcg tat cgg tgg gga aag ccg      2587
Gly Arg Pro Leu Gln Ile Phe Val Asp Ala Tyr Arg Trp Gly Lys Pro
            620             625             630 gtc ggt gtg tgt ggt ggg aag tcg agc gag gtg ttg gat gcg gcg gat      2635
Val Gly Val Cys Gly Gly Lys Ser Ser Glu Val Leu Asp Ala Ala Asp
            635             640             645 gtt ccg gaa aat ggg gac ggg gtg tat tcg gag gag tcg gtg gac aag      2683
Val Pro Glu Asn Gly Asp Gly Val Tyr Ser Glu Glu Ser Val Asp Lys
            650             655             660 ttt gtg gag gag ttt gag aag ggg ttg gct act ttc agg gtg agt ctt      2731
Phe Val Glu Glu Phe Glu Lys Gly Leu Ala Thr Phe Arg Val Ser Leu
            665             670             675 ggt gcc ttt gtt ttt tga                                              2749
Gly Ala Phe Val Phe
680

<210> SEQ ID NO 4
<211> LENGTH: 716
<212> TYPE: PRT
<213> ORGANISM: Humicola grisea

<400> SEQUENCE: 4

Met Asn Arg Val Thr Asn Leu Leu Ala Trp Ala Gly Ala Ile Gly Leu
        -30             -25             -20

Ala Gln Ala Thr Cys Pro Phe Ala Asp Pro Ala Ala Leu Tyr Arg Arg
        -15             -10             -5              -1

Gln Asp Thr Thr Ser Gly Gln Ser Pro Leu Ala Ala Tyr Glu Val Asp
1               5               10              15

Asp Ser Thr Gly Tyr Leu Thr Ser Asp Val Gly Gly Pro Ile Gln Asp
            20              25              30

Gln Thr Ser Leu Lys Ala Gly Ile Arg Gly Pro Thr Leu Leu Glu Asp
            35              40              45

Phe Met Phe Arg Gln Lys Ile Gln His Phe Asp His Glu Arg Val Pro
50              55              60

Glu Arg Ala Val His Ala Arg Gly Ala Gly Ala His Gly Thr Phe Thr
65              70              75              80

Ser Tyr Ala Asp Trp Ser Asn Ile Thr Ala Ala Ser Phe Leu Asn Ala
            85              90              95

Thr Gly Lys Gln Thr Pro Val Phe Val Arg Phe Ser Thr Val Ala Gly
            100             105             110

Ser Arg Gly Ser Ala Asp Thr Ala Arg Asp Val His Gly Phe Ala Thr
            115             120             125

Arg Phe Tyr Thr Asp Glu Gly Asn Phe Asp Ile Val Gly Asn Asn Ile
130             135             140

Pro Val Phe Phe Ile Gln Asp Ala Ile Gln Phe Pro Asp Leu Ile His
145             150             155             160

Ser Val Lys Pro Ser Pro Asp Asn Glu Ile Pro Gln Ala Ala Thr Ala
            165             170             175

His Asp Ser Ala Trp Asp Phe Phe Ser Gln Gln Pro Ser Ala Met His
            180             185             190

Thr Leu Phe Trp Ala Met Ser Gly His Gly Ile Pro Arg Ser Tyr Arg
            195             200             205

His Met Asp Gly Phe Gly Val His Thr Phe Arg Phe Val Lys Asp Asp
            210             215             220

Gly Ser Ser Lys Leu Ile Lys Trp His Phe Lys Ser Arg Gln Gly Lys
```

```
            225                 230                 235                 240
    Ala Ser Leu Val Trp Glu Glu Ala Gln Val Leu Ser Gly Lys Asn Ala
                        245                 250                 255

Asp Phe His Arg Gln Asp Leu Trp Asp Ala Ile Glu Ser Gly Asn Gly
                        260                 265                 270

Pro Glu Trp Asp Val Cys Val Gln Ile Val Asp Glu Ser Gln Ala Gln
                        275                 280                 285

Ala Phe Gly Phe Asp Leu Leu Asp Pro Thr Lys Ile Ile Pro Glu Glu
                        290                 295                 300

Tyr Ala Pro Leu Thr Lys Leu Gly Leu Leu Lys Leu Asp Arg Asn Pro
    305                 310                 315                 320

Thr Asn Tyr Phe Ala Glu Thr Glu Gln Val Met Phe Gln Pro Gly His
                        325                 330                 335

Ile Val Arg Gly Val Asp Phe Thr Glu Asp Pro Leu Leu Gln Gly Arg
                        340                 345                 350

Leu Phe Ser Tyr Leu Asp Thr Gln Leu Asn Arg Asn Gly Gly Pro Asn
                        355                 360                 365

Phe Glu Gln Leu Pro Ile Asn Met Pro Arg Val Pro Ile His Asn Asn
                        370                 375                 380

Asn Arg Asp Gly Ala Gly Gln Met Phe Ile His Arg Asn Lys Tyr Pro
    385                 390                 395                 400

Tyr Thr Pro Asn Thr Leu Asn Ser Gly Tyr Pro Arg Gln Ala Asn Gln
                        405                 410                 415

Asn Ala Gly Arg Gly Phe Phe Thr Ala Pro Gly Arg Thr Val Ser Gly
                        420                 425                 430

Ala Leu Val Arg Glu Val Ser Pro Thr Phe Asn Asp His Trp Ser Gln
                        435                 440                 445

Pro Arg Leu Phe Phe Asn Ser Leu Thr Pro Val Glu Gln Gln Phe Leu
                        450                 455                 460

Val Asn Ala Met Arg Phe Glu Ile Ser Leu Val Lys Ser Glu Glu Cys
    465                 470                 475                 480

Arg Lys Asn Val Leu Thr Gln Leu Asn Arg Val Ser His Asp Val Ala
                        485                 490                 495

Val Arg Val Ala Ala Ala Ile Gly Leu Ala Ala Pro Asp Ala Asp Asp
                        500                 505                 510

Thr Tyr Tyr His Asn Asn Lys Thr Ala Gly Val Ser Ile Leu Gly Ser
                        515                 520                 525

Gly Pro Leu Pro Thr Ile Lys Thr Leu Arg Val Gly Ile Leu Ala Thr
                        530                 535                 540

Thr Ser Glu Ser Ser Ala Leu Asp Gln Ala Ala Gln Leu Arg Thr Arg
    545                 550                 555                 560

Leu Glu Lys Asp Gly Leu Val Val Thr Val Ala Glu Thr Leu Arg
                        565                 570                 575

Glu Gly Val Asp Gln Thr Tyr Ser Thr Ala Asp Ala Thr Gly Phe Asp
                        580                 585                 590

Gly Val Val Val Asp Gly Ala Ala Leu Phe Ala Ser Thr Ala
                        595                 600                 605

Ser Ser Pro Leu Phe Pro Thr Gly Arg Pro Leu Gln Ile Phe Val Asp
                        610                 615                 620

Ala Tyr Arg Trp Gly Lys Pro Val Gly Val Cys Gly Gly Lys Ser Ser
    625                 630                 635                 640

Glu Val Leu Asp Ala Ala Asp Val Pro Glu Asn Gly Asp Gly Val Tyr
                        645                 650                 655
```

```
Ser Glu Glu Ser Val Asp Lys Phe Val Glu Phe Glu Lys Gly Leu
            660                 665                 670

Ala Thr Phe Arg Val Ser Leu Gly Ala Phe Val Phe
        675                 680

<210> SEQ ID NO 5
<211> LENGTH: 31
<212> TYPE: PRT
<213> ORGANISM: Penicillium pinophilum

<400> SEQUENCE: 5

Asp Asp Ser Asn Ala Ser Ser Glu Thr Glu Ala Phe Leu Ser Glu Phe
1               5                   10                  15

Tyr Leu Asn Asp Asn Asp Ala Tyr Leu Thr Thr Asp Val Gly Gly
            20                  25                  30

<210> SEQ ID NO 6
<211> LENGTH: 26
<212> TYPE: DNA
<213> ORGANISM: Artificial Sequence
<220> FEATURE:
<223> OTHER INFORMATION: primer : P catalase F
<220> FEATURE:
<221> NAME/KEY: misc_feature
<222> LOCATION: (18)..(18)
<223> OTHER INFORMATION: n may be any base

<400> SEQUENCE: 6
gaggccggca actacccnga rtggra                                        26

<210> SEQ ID NO 7
<211> LENGTH: 25
<212> TYPE: DNA
<213> ORGANISM: Artificial Sequence
<220> FEATURE:
<223> OTHER INFORMATION: primer : P catalase R

<400> SEQUENCE: 7
cctgctcggt ctcggcraar wartt                                         25

<210> SEQ ID NO 8
<211> LENGTH: 21
<212> TYPE: DNA
<213> ORGANISM: Artificial Sequence
<220> FEATURE:
<223> OTHER INFORMATION: primer : PCNF

<400> SEQUENCE: 8
atgcgaggat tatactccct c                                             21

<210> SEQ ID NO 9
<211> LENGTH: 21
<212> TYPE: DNA
<213> ORGANISM: Artificial Sequence
<220> FEATURE:
<223> OTHER INFORMATION: primer : PCNR

<400> SEQUENCE: 9
ctactcatcc acagcgaatc g                                             21

<210> SEQ ID NO 10
<211> LENGTH: 20
<212> TYPE: PRT
<213> ORGANISM: Humicola grisea
```

-continued

<400> SEQUENCE: 10

Gln Asp Thr Thr Ser Gly Gln Ser Pro Leu Ala Ala Tyr Glu Val Asp
1               5                   10                  15

Asp Ser Thr Gly
            20

<210> SEQ ID NO 11
<211> LENGTH: 17
<212> TYPE: DNA
<213> ORGANISM: Artificial Sequence
<220> FEATURE:
<223> OTHER INFORMATION: primer : H catalase F
<220> FEATURE:
<221> NAME/KEY: misc_feature
<222> LOCATION: (3)..(3)
<223> OTHER INFORMATION: n may be any base
<220> FEATURE:
<221> NAME/KEY: misc_feature
<222> LOCATION: (6)..(6)
<223> OTHER INFORMATION: n may be any base
<220> FEATURE:
<221> NAME/KEY: misc_feature
<222> LOCATION: (12)..(12)
<223> OTHER INFORMATION: n may be any base

<400> SEQUENCE: 11
gtncgnttyt cnactgt                                                17

<210> SEQ ID NO 12
<211> LENGTH: 20
<212> TYPE: DNA
<213> ORGANISM: Artificial Sequence
<220> FEATURE:
<223> OTHER INFORMATION: primer : H catalase R
<220> FEATURE:
<221> NAME/KEY: misc_feature
<222> LOCATION: (6)..(6)
<223> OTHER INFORMATION: n may be any base
<220> FEATURE:
<221> NAME/KEY: misc_feature
<222> LOCATION: (9)..(9)
<223> OTHER INFORMATION: n may be any base
<220> FEATURE:
<221> NAME/KEY: misc_feature
<222> LOCATION: (12)..(12)
<223> OTHER INFORMATION: deoxyinosine

<400> SEQUENCE: 12
aaraanacng gnttrttgtt                                             20

<210> SEQ ID NO 13
<211> LENGTH: 21
<212> TYPE: DNA
<213> ORGANISM: Artificial Sequence
<220> FEATURE:
<223> OTHER INFORMATION: primer : HCNF

<400> SEQUENCE: 13
atgaacagag tcacgaatct c                                           21

<210> SEQ ID NO 14
<211> LENGTH: 21
<212> TYPE: DNA
<213> ORGANISM: Artificial Sequence
<220> FEATURE:
<223> OTHER INFORMATION: primer : HCNR

<400> SEQUENCE: 14
tcaaaaaaca aaggcaccaa g                                           21

<210> SEQ ID NO 15
<211> LENGTH: 21
<212> TYPE: DNA
<213> ORGANISM: Artificial Sequence
<220> FEATURE:
<223> OTHER INFORMATION: primer : proctaseB-N

<400> SEQUENCE: 15
atggtcgtct tcagcaaaac c                                              21

<210> SEQ ID NO 16
<211> LENGTH: 21
<212> TYPE: DNA
<213> ORGANISM: Artificial Sequence
<220> FEATURE:
<223> OTHER INFORMATION: primer : proctaseB-C

<400> SEQUENCE: 16
ctaagcctga gcggcgaatc c                                              21

<210> SEQ ID NO 17
<211> LENGTH: 25
<212> TYPE: DNA
<213> ORGANISM: Artificial Sequence
<220> FEATURE:
<223> OTHER INFORMATION: primer : proctaseBNxba

<400> SEQUENCE: 17
ggtctagaat gtcaagcaag agagt                                          25

<210> SEQ ID NO 18
<211> LENGTH: 26
<212> TYPE: DNA
<213> ORGANISM: Artificial Sequence
<220> FEATURE:
<223> OTHER INFORMATION: primer : proctaseBCxba

<400> SEQUENCE: 18
ggtctagaat caaccactga agtgga                                         26

<210> SEQ ID NO 19
<211> LENGTH: 35
<212> TYPE: DNA
<213> ORGANISM: Artificial Sequence
<220> FEATURE:
<223> OTHER INFORMATION: primer : PCN-XbaIPtN

<400> SEQUENCE: 19
ggtctagagg tcaaaatgcg aggattatac tccct                               35

<210> SEQ ID NO 20
<211> LENGTH: 30
<212> TYPE: DNA
<213> ORGANISM: Artificial Sequence
<220> FEATURE:
<223> OTHER INFORMATION: primer : PCN-XbaIPtC

<400> SEQUENCE: 20
ggtctagact actcatccac agcgaatcgg                                     30

<210> SEQ ID NO 21
<211> LENGTH: 9728
<212> TYPE: DNA
<213> ORGANISM: Artificial Sequence
<220> FEATURE:

<223> OTHER INFORMATION: plasmid pPTPCN

<400> SEQUENCE: 21

```
tcgagattct ggtcccgcgc gaccacctca agcatgcccc tgtccggacg tgctttcgta      60
ttctgtcggg gatgattttc atcttgaagg taggcccctt cggttccccc gtaggccgtg     120
gctctgctga caatttttcca gactttcacg ctcggtgcca agaagacga tgtgcgtgtg     180
tcgctggacc tccaggatcg caccattgaa gccttgaaga cctgcgtagt cgacgatgtt     240
cacctaaacc acgcgattgc gcgattgttg gaattgctca ccaccagcat tcgcacgcgt     300
tttctgcgtt tcgcgccctt ggaccgcagc ggcgatggcg aacaagaacg cccatccgca     360
ccagtctcac ggcatcagtc gccgcggccg cgtgaagggc acaaaaccg ccgggaaggg      420
tcggcgcatg cctggacgcc agcgcagagt gcgacacaaa atctgggata tgtcgatagc     480
aatagccaga cggggaccag catgacttct gtccatgatc cgctggccgg catccctgcc     540
cagccgatca attcgtccaa catcaatgtc tcgttcatgc ccctcctcc atcagtgtat      600
tacaactact acgaccccag cgcaactccg ccggcgggcg agctggacgg gtctaatgtt     660
ccgtctcagg cgatgcacga taatccaggt acgtccggcg gattgcccga ctggtttgcg     720
ctgccactcg accagttttt caacagttcg acagccgtgg tggaccaggg tctgggaggc     780
acgggcccca tggtgggcga atttgacatg ctggaggtgc ttctaaatga acagtatgac     840
ggtcatgagg ggatagagtc ggctggcgga gggaaccttc cgtcacagtt tttgcaatcg     900
tgatcaccga tggtctcatg aatgtacgaa tttacgcgtc gtagcttctt cctcttttg      960
cttggattct tgctagttcc tttctgtaca cttccgcttt tggcttgtga tcttgattgc    1020
tagagatgta tatcctcacg gataccgccg gagtgcgcca tttctggtta ccttctcttt    1080
ccctttttgt ctcgatcgtg aggcggaacg caggatgaag acacggcttc tccatcgcgg    1140
cccaccaacc aacaatgtcc ttggacgccc aactctccat ctactggtca ttggtccaat    1200
gcagagacac cgtcgagctc aaatgggccg gccaaccccg agtcgtcagg ggcagcggca    1260
gcaacgagct aaattagacc actgataaga cgcgatagtc caaagtctga ccgtcacatt    1320
gtgccagcag ataagttgaa tcgtgtgact ggatgttggc taacgtatgg cgtctccgga    1380
ggcccgacgg accctgcgcg atcggcggtg gagcgcaatc taaggacatc cgcgcctaag    1440
atatctaccc ttcagcagtt cagcctagcc ctgcagactt gtcggaccag tgctatcgtg    1500
atcggcccccc acggtcgaat gagctcttgt ctcttttccgt cagaccctgc cagttaatct    1560
gctatctact ccgcggtaac atcgtgcctg tctccactaa ggcagggtcc agggctgtat    1620
gtcttacttt gcaccgagtc ggccgccggt tggctctgtc ttggcaattg cgaatatcct    1680
cacgggcgac ggacgacacg gatttggacg gacatgcgga gatcttcgtc ggtttattcc    1740
tggaagggac atcatctcct tccatcatga cggctgccat agcggggact ctgagacatt    1800
tttgctctga agagcatggt cgacttggat gatggaggag ttgatcgagg tcaatgagga    1860
gaggcttgca agtataagaa gagactgctc gaccagcaga atggatcttc ttgttcatca    1920
accaagagtc caaggcttct ttgtctggtt ctatctcttc tccgaactct cttgcttgac    1980
attctagagg tcaaaatgcg aggattatac tccctcggcg ccttcgccag tctcattgcg    2040
gcggcttcgg ctgcatgccc aatgctgact ggcgaaatcc cagctggtag tgttgccaat    2100
cctcatcatc acggaaagcg tgacgattca aatgcttcct ccgaaacaga agcctttctg    2160
tccgagttct acctcaacga caacgatgcc tatctcacca ccgatgtagg cggtccgatc    2220
gaggatcaaa acagtttgaa ggccggcatt cgtggatcga ccctcttgga agacttcatc    2280
```

```
ttccgtcaga aaatccagca ttttgatcat gagcgtgtag gttatccatt ctatcacgta    2340
cttcaggggt agttctgaca tgcccaggtc ccggaacgtg ccgtgcatgc tcgaggtgca    2400
ggtgctcatg gtgtatttac ttcatatgcc gactggtcca acatcactgc tgcttcattt    2460
ttgggagctt ccggaaagga aacgcccaca tttgtccgct tctcgactgt tgcaggcagc    2520
cgaggaagtg ccgacaccgc tcgtgacgtt cacggatttg ctactcgctt ctatactgac    2580
gagggaaact atggtagcct ttctctttga ctcgtccata gatagggatg taactgactt    2640
caacagacat tgttggaaac aacattcctg tcttcttcat ccaagatgct atcttattcc    2700
cagatctcat ccatagcgtt aagccacagc cagccaatga atcccacag gctgctactg     2760 cacacgacac ggcctatgac ttctttggtc aacagccaag cactctgcat accctcttct    2820
gggcaatggc aggccatggt atcccacggt cttccgtca tgttgacgga ttcggtgtcc     2880
acacctatcg gttcgtgaca gatgatggct cgtccaagtt ggtcaaattt cactggacat    2940
cgctgcaagg tcgggccagt ctggtctggg aggaagctca ggccactgct ggcaaaaatg    3000
ccgactttat gagacaggat ctgtatgata gcattgaggc tggccgttat ccagagtggg    3060
aggtatgtac caccgaattc atggaaagta ctcgactaac gtgaacagct cggcgtgcaa    3120
ataattgagg agtcggatgt cttaagctac ggatttgacc tgttggatcc aaccaagatt    3180
cttccggttg aaaaagttcc aattactgcg ctcggaaaaa tgcaactcaa ccgtaatcca    3240
ttgaattact ttgccgagac agagcaagtc atggtaagtc gaccttccgg cactcgagtc    3300
atttcctact aacgtggata gttccaacct ggccacattg ttcgtggtat cgacttcacc    3360
gaggatcctc ttctccaggg tcgtttattc tcctacctcg atactcagct gaatcgcaat    3420
ggtggtccca actttgaaca aattccaatc aatcgtccgc gtgttcctat ccacaacaac    3480
aaccgcgatg gattcgccca atgtttatt cctttgaacc aggcagcata ttcacccaac     3540
accttgaata tggctctcc tcgacaagcc aacgagactg tcggaaatgg cttctttacc     3600
gcccccgggc gctccgcaga tggacacctt gttcgcgcta cgagcccaac atttgccgac    3660
gtgtggtctc agcctggctt gttttacaac tccttgacgg ctaccgaaca acagttcgtg    3720
atcaatgctt tgcgtttcga attgtctaat gtaaagagcg aggatgttaa aagcaatttc    3780
atcacacaga taaatcgcgt aaacaacacg ttagcaacac ttgtggcttc tgcaattgga    3840
gtctccgcgc ccgaacccga ctctacatac taccacagca taagacgtc taatgtcgga     3900 acattcggta ctccgttgaa aaagcttgac ggtctcaagg tcggagtcct tgcttcggtg    3960
aacggtgaaa gtagtattgc cgagggacaa gcattggcac aaagcctagc gggctcgaac    4020
gtggacgtcg ttatcgtcgc cgagcatctt acttcgaacg tgtcagctac atactctgga    4080
tcagacgcaa cgaactttga tgctgttatt gtcagctcag gggctgaagg tctcttttga   4140
cctcaaacct ttacagccga atccaataca acactttatc cggcaggccg tcctagccag    4200
attttggtcg atgccttccg ctttggcaag ccggttggag cagttggtgg tgccagtgca    4260
gctctgtcag cggtggatat cagtactgat cgtagtggtg tgattactgg tgattccgtc    4320
agtgacgact ttgtcaagca gctaacggag gaccttgcca cattcaaatt cttggaccga    4380
ttcgctgtgg atgagtagtc tagaatcaac cactgaagtg gagtctataa tctgctgatt    4440
gatccctcga cgatgaacta catgtggaaa tgtatagcag acgagggtga tggtgatgat    4500
gttgatttga tgatgacccg tacatacttg atgaagctcg gtacatatgc aaatgtgact    4560
gtatctatgt gatgaatata tatatatata tgtatatcca tctcatggct tttggctatg    4620
```

```
agtgcaggat aaacacctga accagtagta gtactttccc acctatatct actgcggtgc    4680
ctcgtccggc ccaacatcac cccagaggtg gccgcagagg agtcttataa gatagctact    4740
atcagttaca acacctctct gacagatgtg aaggagtaca ataaatcacc gaaacacaaa    4800
ttcaactaaa atcggtaagt aataataatt taagacccaa tccacgcaat gttaaactat    4860
ctctggtgtt gaaagatctc tcccctggca acacctagtt gtgggagaac tgtgtttgcc    4920
tgcctatagt tccgttgacg ctccgtggga aagtgcagtt acataaatat attaagaaag    4980
tagagttgta gtttagatta ttaataagtt tcaatagtct agtcctctac aatcgcacag    5040
ttaaaatatt atcatgtcaa taagcaaaac tgccatagag atagtagtaa gttcctggcg    5100
aagaagttgt gaacttgcct ggaattgaga aaattgggga cgggcgcgtt agatagggac    5160
cgacgcccaa atgaaccaca tcaaataagt caattttttgg aaaccgtttc tacacaagta    5220
gcccttgtgg cgcaatcggt agcgcgtaag acttctaatc ttaaggctgt gggttcgacc    5280
cccaccaggg gcttttttt atttatcttt ttccccttg atttcgcatt caacttcaag    5340
cttttttgaa acatatgagg cgcctcctt atgtcctttt cctttcctt tttcttttctt    5400 atgtcatctc gtccttctgc tatcaatcaa agaaatatct gccctctcca acgtgactt    5460 gtttgcgcaa ttaacatcat gcttcatatt cacatgaacg gcccgctcac ttgctttttt    5520
tgtctaacct caagcaagaa gctgctgtga atgcaagcta atatggcatg atattgtacc    5580
cgccattaac caaggaggcc cttgtggcgc aatcggtagc gcgtaagact tctaatctta    5640
aggctgtggg ttcgacccc accagggggct ttacatttttt ttcatttct ttttggtaca    5700 ttccttcctt attttttcgta gtattacctt aagaaactat aattgactaa ctgggctggg    5760
tcatgataat gttattgaca gtatactgcc tagcaagatg gtgttttata atatcaatca    5820
gctcctcccc cccttcctcc ggcgaatttc gagatagacg ctgaatgttc actgcaacaa    5880
aggaaaggga aggaagaggg ggggcgggta catggaaaat cacatcaaca cacgattaac    5940
gaggcagtgg actggtatgt gccccacgcc taaatcgttc aagcaaagga tgagcagtat    6000
tttcattacc aatgtggata aaccgtctcg ggaactgcga gatctcttcc aatgatttct    6060
tctccagaac ctccacgaag gtgttcgcct tgaataccat acccatggcc gaatttgttg    6120
catagtatac cacttcacga ccgaaggaat cggtgtatct aatccggaaa gctagacgga    6180
gggccggatc atcatgagct tcagagcttg aggttgcata tagacttgta tgcgtttctc    6240
cccaaggaca aagctccagt ttgacaaaga cctttccatc catgatatcc atatcatccg    6300
ggaatagaat ctcgcaatag taaatattag aagctaagtt gagacgatac agccccaagc    6360
ttcaggtaag tgagtagcca gtataagatt aaatcgagct aatagcctgg gagcatacgg    6420
taagcccaaa gagatcatat actgatcatt agtgatgtga ctccatttgg caattcctct    6480
cgtttaaaac gctgatagga taaaaccatt aatactagta tcgcagtatc acgaagtatc    6540
gggtatgaat cctcaaacaa ctccagcgga gagagtagta tcgtcccatg ccttaggcga    6600
attcactggc cgtcgtttta caacgtcgtg actgggaaaa ccctggcgtt acccaactta    6660
atcgccttgc agcacatccc cctttcgcca gctggcgtaa tagcgaagag gcccgcaccg    6720 atcgccctt ccaacagttg cgcagcctga atggcgaatg cgcctgatg cggtattttc    6780 tccttacgca tctgtgcggt atttcacacc gcatacgtca aagcaaccat agtacgcgcc    6840
ctgtagcggc gcattaagcg cggcgggtgt ggtggttacg cgcagcgtga ccgctacact    6900
tgccagcgcc ttagcgcccg ctcctttcgc tttcttccct tcctttctcg ccacgttcgc    6960
cggctttccc cgtcaagctc taaatcgggg gctcccttta gggttccgat ttagtgcttt    7020
```

```
acggcacctc gaccccaaaa aacttgattt gggtgatggt tcacgtagtg ggccatcgcc    7080
ctgatagacg ttttttcgcc ctttgacgtt ggagtccacg ttctttaata gtggactctt    7140
gttccaaact ggaacaacac tcaactctat ctcgggctat tcttttgatt tataagggat    7200
tttgccgatt tcggtctatt ggttaaaaaa tgagctgatt taacaaaaat ttaacgcgaa    7260
ttttaacaaa atattaacgt ttacaatttt atggtgcact ctcagtacaa tctgctctga    7320
tgccgcatag ttaagccagc cccgacaccc gccaacaccc gctgacgcgc cctgacgggc    7380
ttgtctgctc ccggcatccg cttacagaca agctgtgacc gtctccggga gctgcatgtg    7440
tcagaggttt tcaccgtcat caccgaaacg cgcgagacga aagggcctcg tgatacgcct    7500
attttatag gttaatgtca tgataataat ggtttcttag acgtcaggtg gcacttttcg    7560
gggaaatgtg cgcggaaccc ctatttgttt atttttctaa atacattcaa atatgtatcc    7620
gctcatgaga caataaccct gataaatgct tcaataatat tgaaaaagga agagtatgag    7680
tattcaacat ttccgtgtcg cccttattcc cttttttgcg gcattttgcc ttcctgtttt    7740
tgctcaccca gaaacgctgg tgaaagtaaa agatgctgaa gatcagttgg gtgcacgagt    7800
gggttacatc gaactggatc tcaacagcgg taagatcctt gagagttttc gccccgaaga    7860
acgttttcca atgatgagca cttttaaagt tctgctatgt ggcgcggtat tatcccgtat    7920
tgacgccggg caagagcaac tcggtcgccg catacactat tctcagaatg acttggttga    7980
gtactcacca gtcacagaaa agcatcttac ggatggcatg acagtaagag aattatgcag    8040
tgctgccata accatgagtg ataacactgc ggccaactta cttctgacaa cgatcggagg    8100
accgaaggag ctaaccgctt ttttgcacaa catgggggat catgtaactc gccttgatcg    8160
ttgggaaccg gagctgaatg aagccatacc aaacgacgag cgtgacacca cgatgcctgt    8220
agcaatggca acaacgttgc gcaaactatt aactggcgaa ctacttactc tagcttcccg    8280
gcaacaatta atagactgga tggaggcgga taaagttgca ggaccacttc tgcgctcggc    8340
ccttccggct ggctggttta ttgctgataa atctggagcc ggtgagcgtg gtctcgcgg    8400
tatcattgca gcactggggc cagatggtaa gccctcccgt atcgtagtta tctacacgac    8460
ggggagtcag gcaactatgg atgaacgaaa tagacagatc gctgagatag gtgcctcact    8520
gattaagcat tggtaactgt cagaccaagt ttactcatat atactttaga ttgatttaaa    8580
acttcatttt taatttaaaa ggatctaggt gaagatcctt tttgataatc tcatgaccaa    8640
aatcccttaa cgtgagtttt cgttccactg agcgtcagac cccgtagaaa agatcaaagg    8700
atcttcttga tccttttttt tctgcgcgt aatctgctgc ttgcaaacaa aaaaaccacc    8760
gctaccagcg gtggtttgtt tgccggatca agagctacca actctttttc cgaaggtaac    8820
tggcttcagc agagcgcaga taccaaatac tgttcttcta gtgtagccgt agttaggcca    8880
ccacttcaag aactctgtag caccgcctac atacctcgct ctgctaatcc tgttaccagt    8940
ggctgctgcc agtggcgata gtcgtgtct taccggggttg gactcaagac gatagttacc    9000
ggataaggcg cagcggtcgg gctgaacggg gggttcgtgc acacagccca gcttggagcg    9060
aacgacctac accgaactga gatacctaca gcgtgagcta tgagaaagcg ccacgcttcc    9120
cgaagggaga aaggcggaca ggtatccggt aagcggcagg gtcggaacag gagagcgcac    9180
gagggagctt ccagggggaa acgcctggta tctttatagt cctgtcgggt ttcgccacct    9240
ctgacttgag cgtcgatttt tgtgatgctc gtcaggggg cggagcctat ggaaaaacgc    9300
cagcaacgcg gcctttttac ggttcctggc cttttgctgg ccttttgctc acatgttctt    9360
```

```
tcctgcgtta tccctgatt ctgtggataa ccgtattacc gcctttgagt gagctgatac    9420
cgctcgccgc agccgaacga ccgagcgcag cgagtcagtg agcgaggaag cggaagagcg    9480
cccaatacgc aaaccgcctc tccccgcgcg ttggccgatt cattaatgca gctggcacga    9540
caggtttccc gactggaaag cgggcagtga gcgcaacgca attaatgtga gttagctcac    9600
tcattaggca ccccaggctt tacactttat gcttccggct cgtatgttgt gtggaattgt    9660
gagcggataa caatttcaca caggaaacag ctatgaccat gattacgcca agcttgcatg    9720
cctgcagg                                                             9728
```

<210> SEQ ID NO 22
<211> LENGTH: 21
<212> TYPE: DNA
<213> ORGANISM: Artificial Sequence
<220> FEATURE:
<223> OTHER INFORMATION: primer : Nia-N

<400> SEQUENCE: 22

```
atggcgactg tcactgaggt g                                                21
```

<210> SEQ ID NO 23
<211> LENGTH: 21
<212> TYPE: DNA
<213> ORGANISM: Artificial Sequence
<220> FEATURE:
<223> OTHER INFORMATION: primer : Nia-C

<400> SEQUENCE: 23

```
ttagaagaaa tgaaggtccg a                                                21
```

<210> SEQ ID NO 24
<211> LENGTH: 6416
<212> TYPE: DNA
<213> ORGANISM: Aspergillus niger var. macrosporus

<400> SEQUENCE: 24

```
tctagacgtc cactcactga ctactgactc ctgactgact agtagtcggc cgatgggacc      60
atttcttttc ttccatcttt tcctgctcgc ccccactgcg gcaaaaagct caacagtccc     120
aggcaatatt acttgctcaa taatccccga taccgtgaat acacgattaa tcacggtcaa     180
ctggagactt cgtaatcctg ctgcatttaa tgggcaatta tcggcggtg gagcccttg       240
gaaactaaag tggatctggc cgctgtcctc ctggggcttg ttttgccatt acagcacaaa     300
ttgtcactag tatcgagttt agtttagtga gtctgcttgc tgctcgggag aggcttgttt     360
ccagttttttt ttttcatgcc tggttttta tacttttttt tttcgggacc aggtctcaag    420
ttcccacatt cccggtagga atgttcgaat gagaagcccg tgttctccct gtctacccga    480
caggaggaca caccaggcca tgactagacc tgctggagag tacggagtat tactattaca    540
tatctctgct tgttagttaa ctcattgttc gaatccaccg gctcccgcgg aaatctctcc    600
ggccgaatgt tggccctcac tcacgccctc cccccaaaa tagatctcaa accaggtgga    660
atacctcctg tttcttctcc gtggacttag taccagatcc cggccgttgc tggtcacacc    720
ccgttgagct aatccaaaag ccggcagttt tgagggttca tctgtcatct ggttttttgag    780
cgattaattt tcccgtagct aaccctgatc ttccccggat gagtgtcttg ctcctctcat    840
ctgccttctg catgtctgt atcggtccta agctatactc gtcttcatcc ctgatattgt    900
ctcatgcctt atttggcacc tcgaggccat tgaaccacat aaacacatac catgcgact    960
gtcactgagg tgctgacaga gcctttcacc gctcaagggg tcaccctcaa gtcgggtccg   1020
```

```
atcaaggtcc accaggagga gttgcctgcc gtggaacttt cagacattcc tctgccgccc    1080
ccgtcaaaag agccaaccga ggtcctcagt atagacaagc caaccccga ttatcatgtt    1140
ccgcgcgacc ctcgccttat cagactgacc ggtgttcatc ccttcaatgt cgagcctcca    1200
ctcacggcgc tgtacgacga aggtactcaa cgtctttcct gccgcccgc tcttttgaa     1260
ctcggcgcaa acttccttgt attcgtagcg atgctcacct gccaataggc ttcttgactt    1320
ccccggaact gttctatgtg agaaatcatg gcccggtacc attggtgaag acgaagata    1380
tccccaattg ggagattagc atcgaagggt aaggaatctc gatttcctca aacatcgcgt    1440
catcatctga caatggatat gcagcctggt ggagaagccg cttgtcctca acttccggga    1500
cattttgcag caatacgatc agatcacagc accaatcact ctcgtctgtg cgggaaacag    1560
acggaaggag cagaatgtgg tcaggaagac caaaggtttc tcatggggtt ctgccggcct    1620
gtcgacggct ctctggactg gcccaatgat ggcagatatc ctacggagtg cgaagccttt    1680
gaggaaagcc aagtatgtct gcatggaggg agctgataag ctggtaagtt accttatcca    1740
tccatgcatg cagtgccctg acagtttgct ttcagccaaa cgggtattac gggacatcga    1800
tcaaactcaa ttgggccatg gatcccaata ggggaatcat gctggcccac aaaatgaatg    1860
gcgaggatct ccgtcctgat cacggccgtc ccttgagggc tgtcgtaccc ggccagatcg    1920
gtggccgaag tgtcaaatgg ctgaagaagc tcattctcac tgatgcgccc agtgataact    1980
ggtaccacat ctatgacaac cgagtattac cgtgagactt gcctatccga ccacaagagt    2040
acgttgtcta actgttatcc aggacaatgg tttcgcctga atgtcgtcc agtgacccaa     2100
cttggtggcg cgacgaccga tatgcgattt atgatcttaa cgtgaactct tctgttgtat    2160
accccgagca taaggaggtg ctggatcttg cgtcggcagg cccgtcgtac aacgtgaaag    2220
gatatgccta tgcaggaggc ggtcggagga ttacgagagt cgaaatatct ttagacaaag    2280
gcaaatgtac gacgatcatt gcgcaaatgt gttgaggcag agctaacatg ttttttagcct   2340
ggcgattggc caacatctca tatgccgaag acaagtatcg tgactttgaa ggggacttgt    2400
ttggtggtag agtggacatg tcctggcgcg agacttgttt ctgctggtgc ttctggtcgc    2460
tggatatcgc cattcctgag ctagaaaata cagatgccat tctcgtgcga gccatggatg    2520
aggccttggc tctccaacca cgcgatatgt attggtctgt tctgggcatg atgaacaatc    2580
cttggttccg ggtcaccatc acgaaggaga acgggactct caggttcgag cacccaacag    2640
atcctactgg gcccggcgga tggatggagc gcgtcaaaaa ggccgggggt gatctggtca    2700
atggttactg gggagaacga caagcaggag aggaaccgac agagcctgag cctgagaagg    2760
agatcaacat gaagaaagag ggcgtgaacc ggattatcga ccttcaagaa ttcaagaaga    2820
actcaagcga tgagaagccc tggttcatcg tgaacggtga agtgtacgac ggcacggcat    2880
tcctggaggg ccatccggga ggagctcaga gtatcatctc gtctgctggc atcgacgttt    2940
ctgaggaatt tttggcaatc cgtacgtcct agggaccttc gaacaatgga aattagaatg    3000
ctgacacacc cacagatagc gaaacagcca aagccatgat gcccgattac catatcggaa    3060
ccatggataa ggcgtccttg gaagcgctca agaacgacaa cgcaccacaa tcggatgaac    3120
ctcgtgcaac attccttcag tcgaaatcat ggacaaaggc aacacttgta aagaggacgg    3180
acgtgtcctg ggacacgcgg attttcactt tccagctcca acacgacaaa caaaccctgg    3240
gtctgcccat tggccagcat ctcatgatca aggtcgccga ccctaccagc aaagaagtca    3300
tcatccgctc atacaccccct atctccgata ccaaccagga aggcaccatg gacctgctgg    3360
```

```
tcaagatcta cttcgacacg cccacagtca aaggtggcaa gatgaccatg gccttagaga    3420
agctcgcgtt gggatcagaa atcgactgca agggtcccac tggtaggttt gagtaccttg    3480
ggaacggcaa gatcttggtg agcgggaaag agcgccatgt tagttctttt aagatgattt    3540
gcggtggaac tggtatcacg ccaatcttcc aagtgctacg tgcggtgatg caggacaagc    3600
aggaccctac gtcatgcgtg gtcctggatg gcaatagaca ggaagaggac atcctctgcc    3660
gcgccgatct ggacgcctat gaagcgttgg atagcaagaa gtgtaaggtg gtacacactt    3720
taaccaaggc tccggacagt tggactggac gccgtggacg tatatcagaa gacctgctga    3780
aggagcacgc cattcccgat ggcaagagca tggtgcttat ctgtggtcca gaggccatgg    3840
aaaagtccgc caggaagatc cttctggagc aaggatgggc ggagtcggac cttcatttct    3900
tctaagggaa gcgcctcctc agtactggaa atagccttcg tcactagtat aggaagacga    3960
cattgttaga tgtatataag aacgctaatt ccacaagaaa tatgtacgaa ctgtgatgtt    4020
tttcaaattt gaaggctaaa attgggctcg aagtgcgcct gcaatatgcg cgagtcagac    4080
gtaggatcgt ctaccagtgt cagaatcgtc tcattcgttt actcacgtca gtcatttaag    4140
acaagtagtc ggtcctgctt tataaggaaa gcgactgtca actaaatggc gtcgcactat    4200
agtcacttca tctccaaacg ggccacacgg agacagtcgc tggcgctttt ctggatgtaa    4260
atgctatacc cgacgtttca aagaaccttg gacacgttct ataccgcgta agcagcgaat    4320
agaggtagaa gttttgtttc actcatccga cgactgacag gttcaacgtc gtggcgcaca    4380
ccaagattcc attcagcgga gagcgagcgt agggaatcct tcgaagatat aacggaggtt    4440
tcgtacgttc atcgtacttt attctaaaac aattccctgc cgtatttctg aatcgcactc    4500
gaaaaggcac ttgaagcaat tcgcaatccg accctattaa tgacgtcttt cagcatatgg    4560
ttagtagtat ggagcagaca acttctccca cggcaacagc ttcaatggat gcaggaaccg    4620
ccagataaac ctgtcaatca tccacagatc atgaccatac agcgggccaa cagtggagtc    4680
tcccgtattc atcgttctta ctcgaacaca gcccaccaaa acctcgtggg aatctcaagt    4740
gacaaccacc agacgacgcg ttggcagcgc gagatcacgc ctcactaaac ccgaaccaga    4800
ctagtgcctc tccccgtcca acgcccggac caccgcttgt tcgggaaacc gaagcggcag    4860
gaattcgccg cggttcaacc aacccgcgga cgagagctct cccctccgtc ccctcagaaa    4920
taacattatt taccttatcc acctctacac acaaagtctc tctttacgca ccaatcaatc    4980
gccatgcccc cgcgcaagaa agccaaactt accccccaaa gcgagaatgc cgagccgtcc    5040
gcaagcacca ctgaccagcc aacaaccgcg gattacgacc cagtgacaga tccctggacg    5100
gacgagcaag agaccgcgtt attgaagggg attataaaat ggaagcctgt cggtacgttg    5160
accgcaaccc ttctccccgc gcgcgcaggg gaaacactat catcggagca gtgtgacgct    5220
aacgcggccc tctttctctt tcaaaaggca tgcacaagca cttccgtatg atcgcgattt    5280
cggagttcat gaaaagccaa ggctatgcgc ccgcgcacgc agaacacaca cggataccgg    5340
ggatatggaa gaagctgggg acattataca atcttccggc tttggatgaa cggctggggtt   5400
gatgccctct ctcatccatg gagattacgt cctttggatt ctggctcgtg ctaacattca    5460
tctaatatta cggaatgagc aggaagattc attgataaca gacaccgccg aggactcaaa    5520
ggaattctac tgcccgttcg aattacccca ggatgaatac ggagaattga tgttcgaacg    5580
gcggctggcg atggaaggaa ccgcatctcc tgatcctagc acgcatgcgg gatcgaggag    5640
ggggagcacg gtggctgata cggacggtgc gtatataata tctctgcctt ggttgtcaac    5700
tggttgttgg ggaaagcgta ctaatcgcaa tcgattcatc tcatacagaa cctcgctctt    5760
```

```
cccccgcgcc atcacgagga cggaagtcag gtcgtggcgg gcgtccagcg ggacgaggga      5820
cgcgttcgtc gcgtcttcat gtggaggtcg aaccgccggc gaagggatcc ggagctgcgg      5880
aggaagaagc ggattctggc gaggagacag gcgcaaatga agaaggcgat gaagatggtt      5940
cggacgctgc gaaggatgat agtgaggtcg atgaggaagc ggaggggggc tcgcctacga      6000
cgcgaagtac gcgtgcccag acatcgagga cgaagcagaa gggcagaggt acagcaggca      6060
cgggaactcg gaggggtcga cggcgtcagc cttgatattg atatgtgctt tctgctgacg      6120
ttcgttggct ctgtctgtaa caaatacgtc gctaatgata ccttgggaga aataggcgtt      6180
ttggtggggc tttgtttgta tgattacttt tctccttctt tgttctacca tccattgttc      6240
ttttgccgga cggtacgcta tgcatactcc gttgatcaag ccattggctt gtatctttct      6300
atctccaacg acgacagttg gagaatagga aatccgagat aggaagtaaa acaacataga      6360
tggcatctaa atacatggga gcacatacaa tagatcacta catatttggg tctaga         6416
```

THERMOSTABLE CATALASE

CROSS-REFERENCE TO RELATED APPLICATIONS

The present application is a divisional of application Ser. No. 12/918,017 filed Aug. 17, 2010, which is U.S. National Stage of International Application No. PCT/JP2009/052729 filed Feb. 18, 2009, which claims priority to Japanese Application No. 2008-036171 filed Feb. 18, 2008, the entire disclosures of which are hereby incorporated by reference.

TECHNICAL FIELD

The present invention relates to thermostable catalases, more particularly, thermostable catalases derived from *Penicillium pinophilum* or *Humicola grisea*, proteins having a thermostable catalase activity, DNAs encoding the proteins, and a process for producing the thermostable catalases.

BACKGROUND ART

Catalase is an enzyme which catalyzes a reaction in which hydrogen peroxide decomposes into water and oxygen. Hydrogen peroxide aqueous solution is widely used as an antiseptic or a disinfectant. After the completion of disinfection, the hydrogen peroxide solution can be easily removed with water, and is spontaneously decomposed as time progresses, and therefore, is widely used as a disinfectant for food. However, it is desired that hydrogen peroxide is completely decomposed and removed after use, because reactive oxygen species generated from any remaining hydrogen peroxide have a possibility of causing cell aging or cancer. Catalase is extremely useful for the decomposition of hydrogen peroxide, because no additional chemical substance is needed for the decomposition. Actually, catalase is used in decomposing and removing hydrogen peroxidase remained after bleaching of cotton or in food. Catalases derived from microorganisms (patent references 1 to 5) and catalases derived from animals, such as porcine or bovine liver catalase, are known.

Among such known catalases, catalase produced by a filamentous fungus *Aspergillus niger* or porcine liver catalase is widely used for industrial use. However, it is known that these catalases exhibit low thermostability and the remaining activity thereof after the treatment at 70° C. for 30 minutes was approximately 10% (patent reference 6). In particular, for the use of textile processing, food processing, or the like, catalase having thermostability higher than those of conventional catalases is desired, because hydrogen peroxide has to be decomposed at a high temperature. As thermostable catalases, catalases produced by *Aspergillus terreus* (patent reference 6), *Acremonium alabamensis* (patent reference 6), *Thermoascus aurantiacus* (patent reference 6), *Scytalidium thermophilum* (patent reference 7), *Humicola insolens* (patent reference 7), and genus *Thermomyces* (patent reference 8) have been reported.

It is known that filamentous fungi have an extremely high activity of secreting proteins, and are suitable as a host to produce a recombinant protein such as enzymes. Therefore, if a thermostable catalase gene can be introduced into a filamentous fungus and the thermostable catalase can be highly expressed as a recombinant protein, it is expected that the thermostable catalase can be produced at extremely high productivity in comparison with a wild type. With respect to the production of recombinant proteins, it has been reported that recombinant proteins could be produced in filamentous fungi classified into genus *Aspergillus* (patent reference 9), *Penicillium* (patent reference 10), *Humicola* (patent reference 11), *Trichoderma* (patent reference 12), or *Acremonium* (patent reference 13).

When a recombinant protein is expressed in these filamentous fungi as a host, all exogenous genes introduced into the host are not necessarily expressed. In general, it is considered preferable that the origin of an exogenous gene to be introduced is related to that of a host as closely as possible, in view of codon usage. For example, in the case that *Humicola insolens* was used as a host to express endoglucanase as a recombinant protein, a significant amount of endoglucanase was expressed when an NCE4 or NCE5 gene derived from *Humicola insolens* was introduced into *Humicola insolens* (patent references 14 and 15). By contrast, little amount of endoglucanase was expressed when an RCE I gene, which was derived from *Rhizopus oryzae* and had an amino acid sequence showing a high identity with those of NCE4 and NCE5, was introduced into *Humicola insolens* (patent reference 16). Further, in the case that *Aspergillus awamori* was used as a host to express glucoamylase as a recombinant protein, the introduction of a glucoamylase gene derived from *Aspergillus niger* resulted in high productivity (4.6 g/L), but the introduction of a glucoamylase gene derived from *Humicola grisea* resulted in low productivity (0.66 g/L) (non-patent reference 1). Furthermore, in the case that α-amylase was expressed as a recombinant protein, the introduction of an α-amylase gene derived from *Aspergillus oryzae* into *Aspergillus oryzae* as a host resulted in high productivity (12 g/L), but the introduction of the α-amylase gene derived from *Aspergillus oryzae* into *Trichoderma viride* resulted in only a productivity of 1 g/L (non-patent reference 1). These results show that, when a significant amount of recombinant protein is to be expressed, it is preferable to introduce a gene derived from a filamentous fungus which is the species same as or related to that of a host.

When a filamentous fungus is used as a host to express a large amount of thermostable catalase as a recombinant protein, it is considered preferable that the origin of a thermostable catalase gene to be introduced is closely related to the filamentous fungus as the host, as described above. However, with respect to the isolation of thermostable catalase genes, only a catalase gene derived from *Thermoascus aurantiacus* (patent reference 17) and a catalase gene derived from *Scytalidium thermophilum* (patent reference 18) have been reported. Thermostable catalase genes have not been isolated from filamentous fungi developed as a host for protein production, such as genus *Aspergillus, Penicillium, Humicola, Trichoderma*, or *Acremonium*, and therefore, it was very difficult to express thermostable catalase as a recombinant protein with high productivity.

[patent reference 1] Japanese Unexamined Patent Publication (kokai) No. 55-135588
[patent reference 2] Japanese Unexamined Patent Publication (kokai) No. 60-083579
[patent reference 3] Japanese Unexamined Patent Publication (kokai) No. 63-003788
[patent reference 4] Japanese Examined Patent Publication (kokoku) No. 49-004956
[patent reference 5] Japanese Unexamined Patent Publication (kokai) No. 2-076579
[patent reference 6] Japanese Unexamined Patent Publication (kokai) No. 5-153975
[patent reference 7] Japanese Translation Publication (Kohyo) No. 6-506347

[patent reference 8] Japanese Unexamined Patent Publication (kokai) No. 10-257883
[patent reference 9] International Publication WO 97/034004
[patent reference 10] International Publication WO 2000/068401
[patent reference 11] International Publication WO 98/003667
[patent reference 12] International Publication WO 98/011239
[patent reference 13] Japanese Unexamined Patent Publication (kokai) No. 2001/017180
[patent reference 14] International Publication WO 98/003640
[patent reference 15] International Publication WO 2001/090375
[patent reference 16] International Publication WO 2000/024879
[patent reference 17] Japanese Unexamined Patent Publication (kokai) No. 2004-261137
[patent reference 18] U.S. Pat. No. 5,646,025
[non-patent reference 1] Norihiro TSUKAGOSHI, Kumikae Tanpakushitsu Seisan-hou (Production of recombinant proteins), Japan Scientific Societies Press, pp. 94-95

DISCLOSURE OF THE INVENTION

Problems to be Solved by the Invention

Under the circumstances, the expression of a large amount of thermostable catalase as a recombinant protein is desired. An object to be solved by the present inventors is to search filamentous fungi belonging to genus *Aspergillus, Penicillium, Humicola, Trichoderma*, and *Acremonium*, which were developed as hosts for producing recombinant proteins, for thermostable catalases; to isolate genes encoding the thermostable catalases; and to express thermostable catalases in large quantity.

Means for Solving the Problems

To solve the object, the present inventors cultivated a number of filamentous fungi belonging to genus *Aspergillus, Penicillium, Humicola, Trichoderma*, and *Acremonium*, which had been developed as hosts for producing recombinant proteins; evaluated the thermostability of catalase contained in each culture liquid obtained; and attempted to find thermostable catalase from the filamentous fungi. As a result, the present inventors found that *Penicillium pinophilum* and *Humicola grisea* produced thermostable catalases.

Next, the present inventors purified thermostable catalase from the culture liquid of *Penicillium pinophilum*, and obtained a thermostable catalase in which a single band was observed at the position of approximately 80 kDa by SDS-polyacrylamide gel electrophoresis (SDS-PAGE) and the N-terminal amino acid sequence was DDS-NASSETEAFLSEFYLNDNDAYLTTDVGG (SEQ ID NO.: 5). Further, the present inventors purified thermostable catalase from the culture liquid of *Humicola grisea*, and obtained a thermostable catalase in which a single band was observed at the position of approximately 80 kDa by SDS-polyacrylamide gel electrophoresis (SDS-PAGE) and the N-terminal amino acid sequence was QDTTSGQSP-LAAYEVDDSTG (SEQ ID NO.: 10).

Furthermore, the present inventors succeeded in cloning genes encoding the above thermostable catalases from genomic DNAs of *Penicillium pinophilum* and *Humicola grisea*, and determining the nucleotide sequences of the genes, and the present invention was completed.

The present invention relates to:
1) a thermostable catalase produced by a microorganism belonging to genus *Penicillium;*
2) the thermostable catalase of 1), wherein the microorganism belonging to genus *Penicillium* is *Penicillium pinophilum;*
3) the thermostable catalase of 1) or 2), having a molecular weight of approximately 80 kDa;
4) a thermostable catalase produced by *Humicola grisea;*
5) the thermostable catalase of 4), having a molecular weight of approximately 80 kDa;
6) a protein selected from the group consisting of:
(i) a protein comprising the amino acid sequence consisting of amino acids 1-692 of SEQ ID NO.: 2,
(ii) a protein comprising an amino acid sequence in which one or plural amino acids are deleted, substituted, or added in the amino acid sequence consisting of amino acids 1-692 of SEQ ID NO.: 2, and having a thermostable catalase activity, and
(iii) a protein comprising an amino acid sequence having a 70% or more identity with that consisting of amino acids 1-692 of SEQ ID NO.: 2, and having a thermostable catalase activity;
7) a protein consisting of the amino acid sequence consisting of amino acids 1-692 of SEQ ID NO.: 2, and having a thermostable catalase activity;
8) the protein of 6) or 7), having the amino acid sequence consisting of amino acids −1 to −42 of SEQ ID NO.: 2, or an amino acid sequence in which one or plural amino acids are deleted, substituted, or added in the amino acid sequence consisting of amino acids −1 to −42 of SEQ ID NO.: 2, at the N-terminal side of the protein;
9) a protein selected from the group consisting of:
(i) a protein comprising the amino acid sequence consisting of amino acids 1-684 of SEQ ID NO.: 4,
(ii) a protein comprising an amino acid sequence in which one or plural amino acids are deleted, substituted, or added in the amino acid sequence consisting of amino acids 1-684 of SEQ ID NO.: 4, and having a thermostable catalase activity, and
(iii) a protein comprising an amino acid sequence having a 70% or more identity with that consisting of amino acids 1-684 of SEQ ID NO.: 4, and having a thermostable catalase activity;
10) a protein consisting of the amino acid sequence consisting of amino acids 1-684 of SEQ ID NO.: 4, and having a thermostable catalase activity;
11) the protein of 9) or 10), having the amino acid sequence consisting of amino acids −1 to −32 of SEQ ID NO.: 4, or an amino acid sequence in which one or plural amino acids are deleted, substituted, or added in the amino acid sequence consisting of amino acids −1 to −32 of SEQ ID NO.: 4, at the N-terminal side of the protein;
12) a DNA selected from the group consisting of:
(i) a DNA encoding the protein of 6) to 8),
(ii) a DNA comprising the nucleotide sequence consisting of nucleotides 1-2403 of SEQ ID NO: 1, and
(iii) a DNA hybridizing under stringent conditions to a DNA consisting of the nucleotide sequence consisting of nucleotides 1-2403 of SEQ ID NO: 1, and encoding a protein having a thermostable catalase activity;
13) a DNA consisting of the nucleotide sequence consisting of nucleotides 1-2403 of SEQ ID NO: 1;
14) a DNA wherein an intron sequence is excised from the DNA of 12) or 13);

15) the DNA of 14), wherein the intron sequence is one or more sequences selected from the nucleotide sequence consisting of nucleotides 322-372, 599-651, 1068-1113, or 1279-1326 of SEQ ID NO: 1;
16) a DNA wherein a nucleotide sequence encoding a signal sequence is excised from the DNA of 12) to 15).
17) the DNA of 16), wherein the nucleotide sequence encoding a signal sequence is that consisting of nucleotides 1-126 of SEQ ID NO: 1;
18) a DNA selected from the group consisting of:
(i) a DNA encoding the protein of 9) to 11),
(ii) a DNA comprising the nucleotide sequence consisting of nucleotides 1-2749 of SEQ ID NO: 3, and
(iii) a DNA hybridizing under stringent conditions to a DNA consisting of the nucleotide sequence consisting of nucleotides 1-2749 of SEQ ID NO: 3, and encoding a protein having a thermostable catalase activity;
19) a DNA consisting of the nucleotide sequence consisting of nucleotides 1-2749 of SEQ ID NO: 3;
20) a DNA wherein an intron sequence is excised from the DNA of 18) or 19):
21) the DNA of 20, wherein the intron sequence is one or more sequences selected from the nucleotide sequence consisting of nucleotides 283-463, 667-747, 771-846, 1008-1160, 1218-1270, or 1842-1895 of SEQ ID NO: 3;
22) a DNA wherein a nucleotide sequence encoding a signal sequence is excised from the DNA of 18) to 21);
23) the DNA of 22), wherein the nucleotide sequence encoding a signal sequence is that consisting of nucleotides 1-96 of SEQ ID NO: 3;
24) an expression vector comprising the DNA of 12) to 17);
25) a host microorganism transformed with the DNA of 12) to 17) or the expression vector of 24);
26) the host microorganism of 25), wherein the host microorganism is a filamentous fungus;
27) the host microorganism of 26), the filamentous fungus is a filamentous fungus belonging to genus *Aspergillus, Penicillium, Humicola, Trichoderma*, or *Acremonium;*
28) a process for producing a thermostable catalase, characterized by cultivating the host microorganism of 25) to 27), and collecting the thermostable catalase from the culture obtained by the cultivation;
29) an expression vector comprising the DNA of 18) to 23);
30) a host microorganism transformed with the DNA of 18) to 23) or the expression vector of 29);
31) the host microorganism of 30), wherein the host microorganism is a filamentous fungus;
32) the host microorganism of 31), the filamentous fungus is a filamentous fungus belonging to genus *Aspergillus, Penicillium, Humicola, Trichoderma*, or *Acremonium*; and
33) a process for producing a thermostable catalase, characterized by cultivating the host microorganism of 30) to 32), and collecting the thermostable catalase from the culture obtained by the cultivation.

Effects of the Invention

According to the present invention, DNAs necessary for efficiently producing thermostable catalase as a recombinant protein can be obtained, and recombinant microorganisms efficiently expressing thermostable catalase can be obtained. Further, thermostable catalase can be efficiently produced at low cost by cultivating the obtained microorganism. Hydrogen peroxide can be efficiently decomposed at low cost, even at high temperature, by treating a solution containing hydrogen peroxide with the thermostable catalase of the present invention.

BEST MODE FOR CARRYING OUT THE INVENTION

Figure 1:
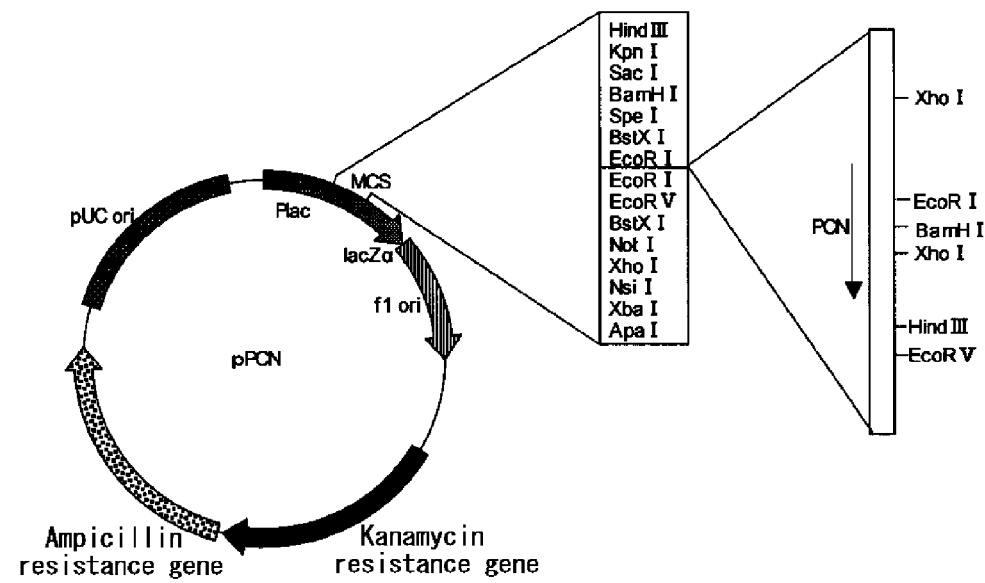
FIG. 1 is a restriction map of plasmid pPCN.
Figure 2:
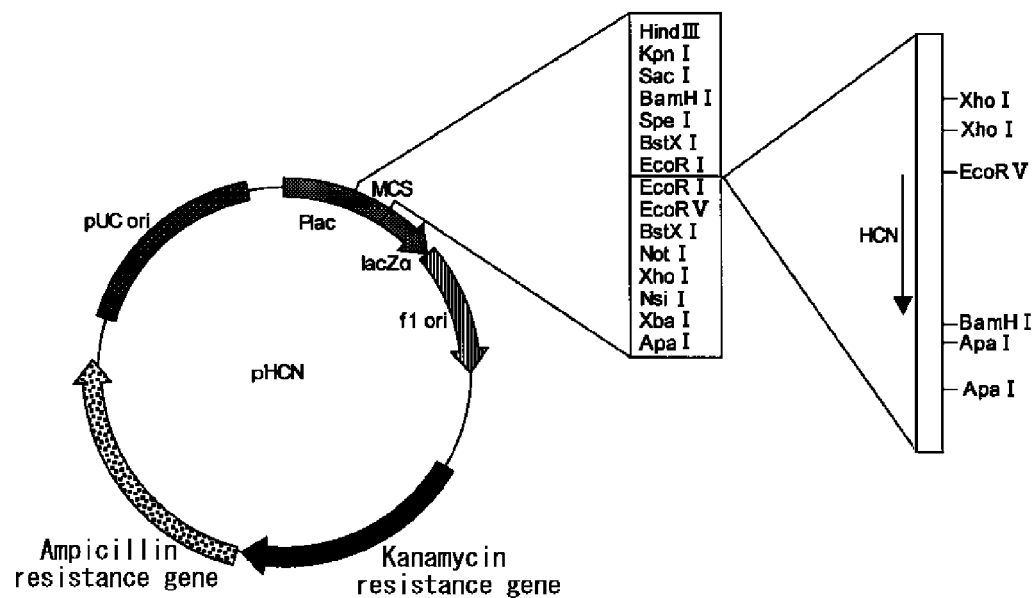
FIG. 2 is a restriction map of plasmid pHCN.

The term "thermostable catalase" as used herein means a catalase in which the percentage of the activity remaining after incubating at 70° C. for 30 minutes is 50% or more, as determined by measuring thermostability in accordance with the method described in Example 4 of patent reference 6.

Thermostable catalase produced by *Penicillium pinophilum* or *Humicola grisea* into a culture liquid may be obtained by, for example, a method disclosed in patent reference 6. A catalase activity may be evaluated by adding catalase to a solution containing hydrogen peroxide and quantifying the decrease in hydrogen peroxide during a predetermined period of time, for example, in accordance with a method disclosed in patent reference 6. Whether or not a catalase is thermostable may be judged, in accordance with a method disclosed in patent reference 6, by heat-treating a culture supernatant, which has been previously diluted to an appropriate concentration, at 70° C. for 30 minutes and measuring the catalase activities before and after the heat-treatment. According to the above definition as used herein, a catalase having a remaining activity of 50% or more after the heat-treatment is regarded as "thermostable catalase".

Culture supernatants of *Penicillium pinophilum* and *Humicola grisea* were obtained by the above method, and the thermostability of catalase contained in each supernatant was determined. As a result, the remaining activities after the heat-treatment at 70° C. for 30 minutes were 50% and 57% with respect to catalases produced by *Penicillium pinophilum* and *Humicola grisea*, respectively, and *Penicillium pinophilum* and *Humicola grisea* produced thermostable catalases.

The thermostable catalases may be purified from the themostable-catalase-containing culture supernatants obtained by the above method in accordance with one or more conventional methods for purifying proteins. As the methods, various commonly known methods may be applied: for example, a combination of hydrophobic chromatography and anion-exchange chromatography may be used. The molecular weight of each purified thermostable catalase may be determined by SDS-PAGE.

In accordance with the above methods, the thermostable catalases produced by *Penicillium pinophilum* and *Humicola grisea* were purified, and the molecular weight of each thermostable catalase was determined. Thermostable catalases having a molecular weight of approximately 80 kDa were obtained from *Penicillium pinophilum* and *Humicola grisea*.

The term "an amino acid sequence in which one or plural amino acids are deleted, substituted, or added in an amino acid sequence" as used herein means that the original amino acid sequence is modified by substitution or the like of plural amino acids which may naturally occur, or in accordance with a well-known method such as site-directed mutagenesis. The number of modified amino acids is preferably 1 to 50, more preferably 1 to 30, still more preferably 1 to 10, still more preferably 1 to 5, most preferably 1 to 2.

Preferred examples of a modified amino acid sequence in the protein according to the present invention may include an amino acid sequence in which one or plural amino acids (preferably one or several amino acids, or one, two, three, or four amino acids) are conservatively substituted.

The term "conservative substitution" as used herein means one or plural amino acid residues are replaced with different amino acids having similar chemical properties. Examples of the conservative substitution include a substitution of a hydrophobic residue for another hydrophobic residue, and a substitution of a polar residue for another polar residue having the same charge. Amino acids which have similar chemical properties and can be conservatively substituted with each other are known to those skilled in the art. More particularly, examples of nonpolar (hydrophobic) amino acids include alanine, valine, isoleucine, leucine, proline, tryptophan, phenylalanine, and methionine. Examples of polar (neutral) amino acids include glycine, serine, threonine, tyrosine, glutamine, asparagine, and cysteine. Examples of basic amino acids having a positive charge include arginine, histidine, and lysine. Examples of acidic amino acids having a negative charge include aspartic acid and glutamic acid.

The term "under stringent conditions" as used herein means that a membrane after hybridization is washed at a high temperature in a solution of low salt concentration, for example, at 60° C. for 15 minutes in a solution of 0.5×SSC concentration (1×SSC: 15 mmol/L trisodium citrate and 150 mmol/L sodium chloride), preferably at 60° C. for 15 minutes in a solution of 0.5×SSC concentration with 0.1% SDS.

Hybridization is carried out in accordance with a known method. When a commercially available library is used, hybridization carried out in accordance with a method described in a protocol attached to the library.

The term "identity" with respect to nucleotide sequences or amino acid sequences as used herein means the degree of similarity between nucleotides or amino acid residues constituting sequences to be compared. The "identity" as used herein may be represented by a value calculated using a known homology search program. For example, the values may be easily calculated by using default parameters in FASTA or the like.

The amino acid sequence having a 70% or more identity with that consisting of amino acids 1-692 of SEQ ID NO.: 2 may be an amino acid sequence having an identity of, preferably 80% or more, more preferably 85% or more, still more preferably 90% or more, still more preferably 95% or more, still more preferably 98% or more, most preferably 99% or more.

The amino acid sequence having a 70% or more identity with that consisting of amino acids 1-684 of SEQ ID NO.: 4 may be an amino acid sequence having an identity of, preferably 80% or more, more preferably 85% or more, still more preferably 90% or more, still more preferably 95% or more, still more preferably 98% or more, most preferably 99% or more.

In the present invention, given the amino acid sequence consisting of amino acids 1-692 of SEQ ID NO.: 2, various nucleotide sequences encoding the amino acid sequence may be easily determined and selected.

In the present invention, given the amino acid sequence consisting of amino acids 1-684 of SEQ ID NO.: 4, various nucleotide sequences encoding the amino acid sequence may be easily determined and selected.

In the present invention, the DNA encoding a protein comprising the amino acid sequence consisting of amino acids 1-692 of SEQ ID NO.: 2 means not only part or all of the nucleotide sequence consisting of nucleotides 1-2403 of SEQ ID NO: 1, but also nucleotide sequences containing degenerate codons encoding the same amino acids. The present invention includes RNA sequences corresponding to these nucleotide sequences.

In the present invention, the DNA encoding a protein comprising the amino acid sequence consisting of amino acids 1-684 of SEQ ID NO.: 4 means not only part or all of the nucleotide sequence consisting of nucleotides 1-2749 of SEQ ID NO: 3, but also nucleotide sequences containing degenerate codons encoding the same amino acids. The present invention includes RNA sequences corresponding to these nucleotide sequences.

Preferred examples of the DNA encoding a protein comprising the amino acid sequence consisting of amino acids 1-692 of SEQ ID NO.: 2 include a DNA comprising the nucleotide sequence consisting of nucleotides 1-2403 of SEQ ID NO: 1.

Preferred examples of the DNA encoding a protein comprising the amino acid sequence consisting of amino acids 1-684 of SEQ ID NO.: 4 include a DNA comprising the nucleotide sequence consisting of nucleotides 1-2749 of SEQ ID NO: 3.

Genes encoding the thermostable catalases produced by *Penicillium pinophilum* and *Humicola grisea* can be isolated by preparing genomic phage libraries from *Penicillium pinophilum* and *Humicola grisea* and obtaining positive phage clones containing the thermostable catalase genes. As probes to screen the genomic phage libraries for positive phage clones, fragments of the thermostable catalase genes may be used. Each of the fragments of the thermostable catalase genes to be used as probes may be amplified by a PCR using each genomic DNA as a template. A primer set for the PCR may be designed based on conserved sequences among known catalase genes derived from filamentous fungi. The nucleotide sequence of each thermostable catalase gene may be determined by subcloning the thermostable catalase gene from an obtained positive clone into an *Escherichia coli* vector and analyzing the nucleotide sequence of the obtained vector. Intron sequences in the determined nucleotide sequence may be deduced on the basis of comparing the amino acid sequence deduced from the nucleotide sequence with those of known catalases, and conserved sequences of introns. Further, a sequence from the translation initiation codon of the gene to the codon immediately upstream of the sequence encoding the N-terminal amino acid sequence of a purified thermostable catalase, may be deduced as a sequence encoding a signal sequence.

The full-length of thermostable catalase gene PCN, which was isolated from genomic DNA of *Penicillium pinophilum* by the method described above, consisted of the 2403-bp nucleotide sequence of SEQ ID NO.: 1, and it was deduced that the gene included four introns having nucleotide sequences consisting of nucleotides 322-372, 599-651, 1068-1113, and 1279-1326 of SEQ ID NO: 1. The amino acid sequence of the thermostable catalase, deduced from the gene sequence, was that of SEQ ID NO.: 2. The amino acid sequence consisting of amino acids 1-31 of SEQ ID NO.: 2 was completely identical with the N-terminal amino acid sequence of the thermostable catalase purified from *Penicillium pinophilum*, and thus, it was deduced that the amino acid sequence consisting of amino acids −1 to −42 of SEQ ID NO.: 2 was a signal sequence and that the nucleotide sequence consisting of nucleotides 1-126 of SEQ ID NO: 1 was a nucleotide sequence encoding the signal sequence.

Based on the nucleotide sequence of catalase gene PCN derived from *Penicillium pinophilum*, primers for amplifying the gene of interest may be designed, a PCR may be carried out using genomic DNA from *Penicillium pinophilum* as a template, an expression vector may be constructed by ligating the amplified DNA fragment into an appropriate vector, and the gene of interest may be isolated. The DNA of the present invention derived from *Penicillium pinophilum* is contained in plasmid pPCN, and thus, the DNA or the plasmid may be used as a DNA template for PCR. An appropriate restriction enzyme may be used to prepare a desired DNA fragment from the plasmid.

According to the present invention, *Escherichia coli* transformed with pPCN is provided. This transformed *Escherichia coli* strain was domestically deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Feb. 7, 2008 (domestic deposit number: FERM P-21504), and was transferred to an international deposit on Dec. 11, 2008 (international deposit number: FERM BP-11074).

The full-length of thermostable catalase gene HCN, which was isolated from genomic DNA of *Humicola grisea* by the method described above, consisted of a 2749-bp nucleotide sequence of SEQ ID NO.: 3, and it was deduced that the gene included six introns having nucleotide sequences consisting of nucleotides 283-463, 667-747, 771-846, 1008-1160, 1218-1270, and 1842-1895 of SEQ ID NO: 3. The amino acid sequence of the thermostable catalase, deduced from the gene sequence, was that of SEQ ID NO.: 4. The amino acid sequence consisting of amino acids 1-20 of SEQ ID NO.: 4 was completely identical with the N-terminal amino acid sequence of the thermostable catalase purified from *Humicola grisea*, and thus, it was deduced that the amino acid sequence consisting of amino acids –1 to –32 of SEQ ID NO.: 4 was a signal sequence and that the nucleotide sequence consisting of nucleotides 1-96 of SEQ ID NO: 3 was a nucleotide sequence encoding the signal sequence.

Based on the nucleotide sequence of catalase gene HCN derived from *Humicola grisea*, primers for amplifying the gene of interest may be designed, a PCR may be carried out using genomic DNA from *Humicola grisea* as a template, an expression vector may be constructed by ligating the amplified DNA fragment into an appropriate vector, and the gene of interest may be isolated. The DNA of the present invention derived from *Humicola grisea* is contained in plasmid pHCN, and thus, the DNA or the plasmid may be used as a DNA template for PCR. An appropriate restriction enzyme may be used to prepare a desired DNA fragment from the plasmid.

According to the present invention, *Escherichia coli* transformed with pHCN is provided. This transformed *Escherichia coli* strain was domestically deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Feb. 7, 2008 (domestic deposit number: FERM P-21503), and was transferred to an international deposit on Dec. 11, 2008 (international deposit number: FERM BP-11073).

Each of the thermostable catalase genes, isolated as described above, may be introduced into a host, and a desired thermostable catalase may be produced by expressing it in the host. The DNA to be introduced into the host may be the full-length of a thermostable catalase gene, a DNA obtained by excising part of all of intron sequences from the full-length DNA, or a DNA obtained by excising the nucleotide sequence encoding a signal sequence.

According to the present invention, an expression vector comprising the DNA of the present invention, in which the DNA can be replicated in a host microorganism and a protein encoded by the DNA can be expressed, is provided. Further, according to the present invention, a microorganism transformed with this expression vector is provided.

The host-vector system is not particularly limited. For example, a system using *Escherichia coli*, actinomycetes, yeasts, or fungi, or a fusion protein expression system using the same may be used. Examples of a preferred host microorganism used in the present invention include filamentous fungi, more preferably genus *Trichoderma*, genus *Aspergillus*, genus *Penicillium* (most preferably *Penicillium pinophilum*), genus *Humicola* (most preferably *Humicola grisea*), and genus *Acremonium*. As an expression vector, expression vectors disclosed in patent references 9 to 13 may be used.

The expression vector of the present invention may be constructed in accordance with procedures and methods widely used in the field of genetic engineering.

The expression vector of the present invention may include not only the DNA of the present invention, but also a DNA capable of regulating the expression of the DNA, a genetic marker to select a transformant, or the like, to express a desired protein by incorporating the expression vector into a host microorganism.

The obtained transformant may be cultivated in an appropriate medium, and the protein of the present invention may be obtained by isolating it from the culture. The cultivation of the transformant and the conditions thereof may be appropriately selected in accordance with the microorganism used. The protein of interest may be collected and purified from the culture liquid in accordance with conventional methods.

EXAMPLES

The present invention now will be further illustrated by, but is by no means limited to, the following Examples.

Example 1

Measurement of Catalase Activity (Thermostability) in Culture Liquid of *Penicillium pinophilum*

*Penicillium pinophilum* grown on potato dextrose agar was inoculated in a 200 mL conical flask containing 30 mL of a medium (50 g/L sucrose, 20 g/L malt extract, and 5 g/L yeast extract), and cultivated at 26° C. for 5 days with shaking. The cells were removed from the resulting culture liquid by centrifugation to obtain the culture supernatant. The catalase activity (thermostability) of catalase contained in the resulting culture supernatant was measured by the method described in Example 4 of patent reference 6. The percentage of the remaining activity after incubating at 70° C. for 30 minutes was 50%. It was concluded from the result that *Penicillium pinophilum* produced thermostable catalase.

Example 2

Isolation and Purification of Thermostable Catalase in Culture Liquid of *Penicillium pinophilum*

Ammonium sulfate was dissolved in the culture supernatant of *Penicillium pinophilum*, obtained in the method described in Example 1, at a final concentration of 1 mol/L. The resulting solution was subjected and adsorbed to a hydrophobic column Phenyl Sepharose HP 26/10 (manufactured by GE Healthcare bioScience), which had been previously equilibrated with a 50 mmol/L phosphate buffer (pH7.0) containing 1 mol/L ammonium sulfate. Proteins adsorbed to the hydrophobic column were eluted and fractionated by a linear gradient elution method from a 50 mmol/L phosphate buffer (pH7.0) containing 1 mol/L ammonium sulfate to a 50 mmol/L phosphate buffer (pH7.0). A catalase activity of each fractionated eluate was measured by the method described in Example 1, and fractions having the activity were collected. Ammonium sulfate was added to the collected active fraction at a final concentration of 1 mol/L, and the above procedure was repeated to carry out rechromatography using the hydrophobic column. The resulting active fraction was concentrated and desalted by ultrafiltration, and adjusted to a final concentration of 50 mmol/L with a phosphate buffer (pH8.0). This solution was subjected to an anion-exchange column MonoQ (manufactured by GE healthcare Bioscience), which had been previously equilibrated with a 50 mmol/L phosphate buffer (pH8.0) containing 1 mol/L ammonium sulfate, and proteins were adsorbed to the column. The adsorbed proteins were eluted and fractionated by a linear gradient elution method from a 50 mmol/L phosphate buffer (pH8.0) to a 50 mmol/L phosphate buffer (pH8.0) containing 1 mol/L NaCl. A catalase activity (thermostability) of each fractionated eluate was measured by the method described in Example 1, and fractions having the activity were collected. The collected active fraction was analyzed by SDS-PAGE to detect a single band of approximately 80 kDa, and it was judged that the protein detected as the band is a thermostable catalase. The thermostable catalase was separated by SDS-PAGE and blotted on a polyvinylidene difluoride (PVDF) membrane. The N-terminal amino acid sequence was analyzed to obtain the following sequence:

```
                                          (SEQ ID NO.: 5)
       DDSNASSETEAFLSEFYLNDNDAYLTTDVGG
```

Example 3

Cloning of Thermostable Catalase Gene PCN from *Penicillium pinophilum*

3-1) Preparation of Genomic DNA Library

Genomic DNA was isolated and purified from *Penicillium pinophilum* cells in accordance with the method of Horiuchi et al. [H. Horiuchi et al., J. Bacteriol., 170, 272-278, (1988)]. The isolated genomic DNA was partially digested with restriction enzyme Sau3AI. The resulting DNA fragments were ligated with BamHI arms of a phage vector EMBL3 cloning kit (manufactured by Stratagene) using a ligation kit Ver. 2 (manufacture by Takara Bio). The mixture was precipitated with ethanol and dissolved in a TE buffer. The whole amount of the ligated mixture and a MaxPlaxA packerging kit (manufactured by Epicenter Technologies) were used to form phage particles, and an *Escherichia coli* XL1-blue MRA (P2) strain was infected with the phage particles. As a result, a genomic DNA library composed of $1.1 \times 10^4$ phages was obtained.

3-2) Preparation of Probe

The following primers ware prepared based on conserved sequences among known catalases:

```
P catalase F:
                                          (SEQ ID NO.: 6)
       GAGGCCGGCAACTACCCNGARTGGRA P catalase R:
                                          (SEQ ID NO.: 7)
       CCTGCTCGGTCTCGGCRAARWARTT
```

The P catalase F and P catalase R primers and genomic DNA were used as primers and a template, respectively, to carry out a PCR. LA Taq polymerase (manufactured by Takara Bio) was used in the PCR. In the PCR, a cycle composed of a reaction at 94° C. for 30 seconds, annealing for 30 seconds, and a reaction at 72° C. for 1 minute was repeated 40 times. In this regard, the annealing temperature in the first 20 cycles was stepwisely lowered from 63° C. to 53° C., and the annealing temperature in the subsequent 20 cycles was 53° C. The amplified DNA fragment of 250 bp was inserted into a pCR2.1-TOPO plasmid vector, using a TOPO TA cloning kit (manufactured by Invitrogen) in accordance with a protocol attached to the kit, to obtain plasmid TOPO-P catalase.

The cloned DNA fragment inserted into plasmid TOPO-P catalase was sequenced using a BigDye® Terminator v3.1 Cycle Sequencing Kit (manufactured by Applied Biosystems) and an ABI PRISM genetic analyzer (manufactured by Applied Biosystems) in accordance with protocols attached thereto. The determined nucleotide sequence was used to carry out a homology search. As a result, the nucleotide sequence showed a 71% identity with that of a catalase derived from *Aspergillus clavatus*, and thus, it was judged that the DNA fragment was part of a catalase gene. The DNA fragment was amplified by a PCR using plasmid TOPO-P catalase in a fashion substantially similar to that described above, and the obtained PCR product was labeled using an ECL direct system (manufactured by Amersham Pharmacia Biotech) as a probe.

3-3) Screening by Plaque Hybridization

Phage plaques prepared in Example 3-1 were transferred to a Hybond N+ Nyron Transfer Membrane (manufactured by Amersham). The membrane was denatured with alkali, washed with 5×SSC (SSC: 15 mmol/L trisodium citrate and 150 mmol/L sodium chloride), and dried to immobilize DNAs. After a prehybridization at 42° C. for 1 hour, the probe labeled with horseradish peroxidase (HRP) was added, and a hybridization at 42° C. for 4 hours was carried out. The probe was washed with 0.5×SSC containing 6 mol/L urea and 0.4% SDS twice, and washed with 2×SSC twice.

After the probe was washed, the nylon membrane was immersed in a detection solution for 1 minute, and exposed to a hyperfilm ECL (manufactured by Amersham) to obtain a positive clone. The preparation of DNA from the positive clone was carried out by using LE392 as a host *Escherichia coli* in accordance with the method of Maniatis et al. (J. Sambrook, E. F. Fritsch and T. Maniatis, "Molecular Cloning", Cold Spring Harbor Laboratory Press. 1989). LE392 was cultivated in an LB-MM medium (1% peptone, 0.5% yeast extract, 0.5% sodium chloride, 10 mmol/L magnesium sulfate, and 0.2% maltose) overnight. The culture was infected with a phage solution derived from a single plaque, and cultivated in the LB-MM medium overnight. Sodium chloride and chloroform were added to the culture at final concentrations of 1 mol/L and 0.8%, respectively, to promote the lysis of *Escherichia coli*. The *Escherichia coli* cell debris was removed by centrifugation, and phage particles were collected from a polyethylene glycol (PEG) precipitate (10% PEG6000). The phage particles were digested with proteinase K in the presence of SDS, treated with phenol, and precipitated with ethanol, to collect phage DNA.

The obtained DNA and the ECL direct system were used to carry out Southern blotting. A hybridization was carried out using the PCR-amplified fragment described in Example 3-2 as a probe. As a result, a PstI fragment of approximately 7 kb showed common hybridization patterns to those of chromosomal DNA.

The PstI fragment was cloned into pUC118 to obtain plasmid pUC-PCN. The nucleotide sequence of the obtained plasmid was determined by the method described in Example 3-2. To subclone catalase gene PCN derived from *Penicillium pinophilum*, a PCR using pUC-PCN as a template and the following primer set (PCNF and PCNR) was carried out to amplify the PCN gene.

```
PCNF:
                               (SEQ ID NO.: 8)
ATGCGAGGATTATACTCCCTC

PCNR:
                               (SEQ ID NO.: 9)
CTACTCATCCACAGCGAATCG
```

The amplified DNA was inserted into a pCR2.1-TOPO plasmid vector using a TOPO TA cloning kit (manufactured by Invitrogen) to obtain plasmid pPCN. An *Escherichia coli* TOP10 strain (Invitrogen) was transformed with plasmid pPCN to obtain *Escherichia coli* TOP10/pPCN.

3-4) Deduction of Amino Acid Sequence of Thermostable Catalase

The full-length of thermostable catalase gene PCN, which was isolated from genomic DNA of *Penicillium pinophilum* by the method described above, consisted of the 2403-bp nucleotide sequence of SEQ ID NO.: 1. On the basis of comparing the amino acid sequence deduced from the nucleotide sequence with those of known catalases, and conserved sequences of introns, it was deduced that the gene included four introns having nucleotide sequences consisting of nucleotides 322-372, 599-651, 1068-1113, and 1279-1326 of SEQ ID NO: 1. The amino acid sequence of the thermostable catalase, deduced from the nucleotide sequence, was that of SEQ ID NO.: 2. The amino acid sequence consisting of amino acids 1-31 of SEQ ID NO.: 2 was completely identical with the N-terminal amino acid sequence (shown in Example 2) of the thermostable catalase purified from *Penicillium pinophilum*, and thus, it was deduced that the amino acid sequence consisting of amino acids −1 to −42 of SEQ ID NO.: 2 was a signal sequence and that the nucleotide sequence consisting of nucleotides 1-126 (encoding the amino acids −1 to −42 of SEQ ID NO.: 2) of SEQ ID NO: 1 was a nucleotide sequence encoding the signal sequence.

Example 4

Measurement of Catalase Activity (Thermostability) in Culture Liquid of *Humicola grisea*

A culture supernatant of *Humicola grisea* was prepared in a fashion substantially similar to that described in Example 1. The catalase activity (thermostability) of catalase contained in the resulting culture supernatant was measured by the method described in Example 1. The percentage of the remaining activity after incubating at 70° C. for 30 minutes was 57%. It was concluded from the result that *Humicola grisea* produced thermostable catalase.

Example 5

Isolation and Purification of Thermostable Catalase in Culture Liquid of *Humicola grisea*

Ammonium sulfate was dissolved in the culture supernatant of *Humicola grisea*, obtained in the method described in Example 4, at a final concentration of 1 mol/L. The resulting solution was subjected and adsorbed to a hydrophobic column Phenyl Sepharose HP 26/10 (manufactured by GE Healthcare bioScience), which had been previously equilibrated with a 50 mmol/L phosphate buffer (pH7.0) containing 1 mol/L ammonium sulfate. Proteins adsorbed to the hydrophobic column were eluted and fractionated by a linear gradient elution method from a 50 mmol/L phosphate buffer (pH7.0) containing 1 mol/L ammonium sulfate to a 50 mmol/L phosphate buffer (pH7.0). A catalase activity of each fractionated eluate was measured by the method described in Example 1, and fractions having the activity were collected. Ammonium sulfate was added to the collected active fraction at a final concentration of 1 mol/L, and the above procedure was repeated to carry out rechromatography using the hydrophobic column. The resulting active fraction was concentrated and desalted by ultrafiltration, and adjusted to a final concentration of 50 mmol/L with an acetate buffer (pH4.0). This solution was subjected to a cation-exchange column MonoS (manufactured by GE healthcare Bioscience), which had been previously equilibrated with a 50 mmol/L acetate buffer (pH4.0). The catalase activity was detected in the non-adsorbed fraction, and thus, the non-adsorbed fraction was collected as the active fraction. The collected active fraction was analyzed by SDS-PAGE to detect a single band of approximately 80 kDa, and it was judged that the protein detected as the band is a thermostable catalase. The thermostable catalase was separated by SDS-PAGE and blotted on a PVDF membrane. The N-terminal amino acid sequence was analyzed to obtain the following sequence: QDTTSGQSPLAAYEVDDSTG (SEQ ID NO.: 10)

Example 6

Cloning of Thermostable Catalase Gene HCN from *Humicola grisea*

6-1) Preparation of Genomic DNA Library

A genomic DNA library of *Humicola grisea* was prepared by the method described in Example 3-1.

6-2) Preparation of Probe

The following primers ware prepared based on conserved sequences among catalases derived from filamentous fungi and yeasts:

```
H catalase F:
                               (SEQ ID NO.: 11)
GTNCGNTTYTCNACTGT H catalase R:
                               (SEQ ID NO.: 12)
AARAANACNGGNTTRTTGTT
```

[The underlined abbreviation "N" at the 12th position of SEQ ID NO.: 12 stands for deoxyinosine.]

The H catalase F and H catalase R primers and genomic DNA were used as primers and a template, respectively, to carry out a PCR. Ex Taq polymerase (manufactured by Takara Bio) was used in the PCR. In the PCR, a cycle composed of a reaction at 98° C. for 10 seconds, annealing at 55° C. for 30 seconds, and an elongation reaction at 72° C. for 15 seconds was repeated 30 times. The amplified DNA fragment of 300 bp was inserted into a pCR2.1-TOPO plasmid vector, using a TOPO TA cloning kit (manufactured by Invitrogen) in accordance with a protocol attached to the kit, to obtain plasmid TOPO-H catalase.

The cloned DNA fragment inserted into plasmid TOPO-H catalase was sequenced, and the determined nucleotide sequence was used to carry out a homology search. As a result, the nucleotide sequence showed a 97% identity with that of a catalase derived from *Sclerotinia sclerotiorum*, and thus, it was judged that the DNA fragment was part of a catalase gene. The DNA fragment was amplified by a PCR using plasmid TOPO-H catalase in a fashion substantially similar to that described above, and the obtained PCR product was labeled using an ECL direct system (manufactured by Amersham Pharmacia Biotech) as a probe.

6-3) Screening by Plaque Hybridization

The genomic DNA library was screened in accordance with the method described in Example 3-3, and a positive clone was obtained. The obtained positive clone was analyzed by Southern blotting. As a result, an XhoI fragment of approximately 7 kb and a BamHI fragment of approximately 4 kb showed common hybridization patterns to those of chromosomal DNA. The XhoI fragment and the BamHI fragment were separately cloned into pUC118 to obtain plasmid pUC-HCN-XhoI and plasmid pUC-HCN-BamHI, respectively. The nucleotide sequences of these plasmids were determined. As a result, the XhoI fragment contained the sequence from the 616th nucleotide to the 3'-terminus of SEQ ID NO.: 3 and the BamHI fragment contained the sequence from the 5'-terminus to the 1675th nucleotide of SEQ ID NO.: 3, and thus, these fragments contained thermostable catalase gene fragments. These nucleotide sequences were joined to determine that of the full-length of a thermostable catalase gene. To subclone catalase gene HCN derived from *Humicola grisea*, a PCR using genomic DNA of *Humicola grisea* as a template and the following primer set (HCNF and HCNR) was carried out to amplify the HCN gene.

```
HCNF:
                        (SEQ ID NO.: 13)
ATGAACAGAGTCACGAATCTC

HCNR:
                        (SEQ ID NO.: 14)
TCAAAAAACAAAGGCACCAAG
```

The amplified DNA was inserted into a pCR2.1-TOPO plasmid vector using a TOPO TA cloning kit (manufactured by Invitrogen) to obtain plasmid pHCN. An *Escherichia coli* TOP10 strain (Invitrogen) was transformed with plasmid pHCN to obtain *Escherichia coli* TOP10/pHCN.

6-4) Deduction of Amino Acid Sequence of Thermostable Catalase

The full-length of thermostable catalase gene HCN, which was isolated from genomic DNA of *Humicola grisea* by the method described above, consisted of the 2749-bp nucleotide sequence of SEQ ID NO.: 3. On the basis of comparing the amino acid sequence deduced from the nucleotide sequence with those of known catalases, and conserved sequences of introns, it was deduced that the gene included six introns having nucleotide sequences consisting of nucleotides 283-463, 667-747, 771-846, 1008-1160, 1218-1270, and 1842-1895 of SEQ ID NO: 3. The amino acid sequence of the thermostable catalase, deduced from the nucleotide sequence, was that of SEQ ID NO.: 4. The amino acid sequence consisting of amino acids 1-20 of SEQ ID NO.: 4 was completely identical with the N-terminal amino acid sequence (shown in Example 5) of the thermostable catalase purified from *Humicola grisea*, and thus, it was deduced that the amino acid sequence consisting of amino acids −1 to −32 of SEQ ID NO.: 4 was a signal sequence and that the nucleotide sequence consisting of nucleotides 1-96 (encoding the amino acids −1 to −32 of SEQ ID NO.: 4) of SEQ ID NO: 3 was a nucleotide sequence encoding the signal sequence.

Example 7

Preparation of Expression Vector for Recombinant PCN

An expression of recombinant PCN using *Aspergillus niger* var. *macrosporus* as a host was carried out by using an expression vector in which the PCN gene was inserted between the promoter and the terminator of a proctase B gene, which was remarkably expressed in *Aspergillus niger* var. *macrosporus*. The expression vector was prepared in accordance with the following procedures.

7-1) Preparation of Genomic DNA Library

Genomic DNA was isolated and purified from *Aspergillus niger* var. *macrosporus* cells in accordance with the method of Horiuchi et al. [H. Horiuchi et al., J. Bacteriol., 170, 272-278, (1988)]. The isolated genomic DNA was partially digested with restriction enzyme Sau3AI. The resulting DNA fragments were ligated with BamHI arms of a phage vector AEMBL3 cloning kit (manufactured by Stratagene) using a ligation kit Ver. 2 (manufacture by Takara Bio). The mixture was precipitated with ethanol and dissolved in a TE buffer. The whole amount of the ligated mixture and a MaxPlaxA packerging kit (manufactured by Epicenter Technologies) were used to form phage particles, and an *Escherichia coli* XL1-blue MRA (P2) strain was infected with the phage particles. As a result, a genomic DNA library composed of $1.25 \times 10^5$ phages was obtained.

7-2) Preparation of Probe

With respect to the genomic DNA library of *Aspergillus niger* var. *macrosporus*, Southern blotting was carried out using the coding region of the proctase B gene as a probe to isolate a clone containing the promoter and terminator regions of the proctase B gene. The coding region of the proctase B was amplified by a PCR using genomic DNA of *Aspergillus niger* var. *macrosporus* as a template and the following primers (proctaseB-N and proctaseB-C), which were designed based on the 5'- and 3'-termini of the coding region of the proctase B disclosed in Japanese Unexamined Patent Publication (kokai) No. 5-68570.

```
proctaseB-N:
                        (SEQ ID NO.: 15)
ATGGTCGTCTTCAGCAAAACC proctaseB-C:
                        (SEQ ID NO.: 16)
CTAAGCCTGAGCGGCGAATCC
```

The PCR was carried out using an LA PCR™ KIT Ver2.1 (manufactured by Takara Bio). In the PCR, after an incubation at 94° C. for 1 minute, a cycle composed of a reaction at 94° C. for 30 seconds, a reaction at 52° C. for 30 seconds, and a reaction at 72° C. for 90 seconds was repeated 30 times, and a reaction at 72° C. for 7 minutes was carried out to complete the PCR. As a result, a DNA of approximately 1.2 kb was amplified. The amplified DNA fragment of 1.2 kb was inserted into a pCR2.1-TOPO plasmid vector, using a TOPO TA cloning kit (manufactured by Invitrogen) in accordance with a protocol attached to the kit, to obtain plasmid TOPO-ProB. The cloned DNA fragment inserted into plasmid TOPO-ProB was sequenced using a BigDye® Terminator v3.1 Cycle Sequencing Kit (manufactured by Applied Biosystems) and an ABI PRISM genetic analyzer (manufactured by Applied Biosystems) in accordance with protocols attached thereto. The determined nucleotide sequence accorded with that of the proctase B gene disclosed in Japanese Unexamined Patent Publication (kokai) No. 5-68570, and thus, it was judged that the DNA fragment was the coding region of the proctase B gene. The DNA fragment was labeled using an ECL direct system (manufactured by Amersham Pharmacia Biotech) as a probe.

7-3) Screening of Clone Containing Promoter and Terminator Regions of Proctase Gene by Plaque Hybridization Phage plaques prepared in Example 7-1 were transferred to a Hybond N+ Nyron Transfer Membrane (manufactured by Amersham). The membrane was denatured with alkali, washed with 5×SSC (SSC: 15 mmol/L trisodium citrate and 150 mmol/L sodium chloride), and dried to immobilize DNAs. After a prehybridization at 42° C. for 1 hour, the probe prepared by the method described in Example 7-2 was added, and a hybridization at 42° C. for 20 hours was carried out. The probe was washed with 0.5×SSC containing 6 mol/L urea and 0.4% SDS twice, and washed with 2×SSC twice. After the probe was washed, the nylon membrane was immersed in a detection solution for 1 minute, and exposed to a hyperfilm ECL (manufactured by Amersham) to obtain eight positive clones.

The preparation of DNA from each of the positive clones was carried out by using LE392 as a host *Escherichia coli* in accordance with the method of Maniatis et al. (J. Sambrook, E. F. Fritsch and T. Maniatis, "Molecular Cloning", Cold Spring Harbor Laboratory Press. 1989). LE392 was cultivated in an LB-MM medium (1% peptone, 0.5% yeast extract, 0.5% sodium chloride, 10 mmol/L magnesium sulfate, and 0.2% maltose) overnight. The culture was infected with a phage solution derived from a single plaque, and cultivated in the LB-MM medium overnight. Sodium chloride and chloroform were added to the culture at final concentrations of 1 mol/L and 0.8%, respectively, to promote the lysis of *Escherichia coli*. The *Escherichia coli* cell debris was removed by centrifugation, and phage particles were collected from a polyethylene glycol (PEG) precipitate (10% PEG6000). The phage particles were digested with proteinase K in the presence of SDS, treated with phenol, and precipitated with ethanol, to collect phage DNA.

The obtained DNA and the ECL direct system were used to carry out Southern blotting. A hybridization was carried out using the probe prepared by the method described in Example 7-2. As a result, an XhoI-EcoRI fragment of approximately 5.5 kb showed common hybridization patterns to those of chromosomal DNA. It was judged that the DNA fragment contained the proctase B gene, and then, subcloning of the DNA fragment was carried out. The XhoI-EcoRI fragment excised from the phage DNA was inserted between the SalI and EcoRI sites of pUC119 to obtain plasmid pPROB/119E.X. The nucleotide sequence of the obtained plasmid was sequenced to determine those of the promoter and terminator regions of the proctase B gene.

7-4) Construction of Recombinant Vector pPTB-EX for Gene Expression

A vector in which the coding region of the proctase B gene was excised from plasmid pPROB/119E.X prepared by the method described in Example 7-3 and the 3'-terminus of the promoter region of the gene was ligated to the 5'-terminus of the terminator region of the gene via the XbaI recognition sequence, was designated expression vector pPTB-EX. The expression vector pPTB-EX was prepared by an inverse PCR using pPROB/119E.X as a template and the following primers (proctaseBNxba and proctaseBCxba) designed based on the 3'-terminus of the promoter and the 5'-terminus of the terminator of the proctase B gene, respectively.

```
proctaseBNxba:
                            (SEQ ID NO.: 17)
GGTCTAGAATGTCAAGCAAGAGAGT proctaseBCxba:
                            (SEQ ID NO.: 18)
GGTCTAGAATCAACCACTGAAGTGGA
```

In this regard, the XbaI recognition sequence was added to the 5'-terminus of each primer. Primestar MAX DNA POLYMERASE (manufactured by Takara Bio) was used in the inverse PCR, in which a cycle composed of a reaction at 98° C. for 10 seconds, a reaction at 55° C. for 5 seconds, and a reaction at 72° C. for 60 seconds was repeated 30 times. As a result, a DNA fragment of approximately 7 kb was amplified. The resulting PCR reaction liquid and a QIAQUICK PCR PURIFICATION KIT (manufactured by Qiagen) were used to purify the DNA fragment. The DNA fragment was dissolved in 50 μL of a TE buffer, digested with restriction enzyme XbaI, and re-ligated using a ligation kit Ver. 2 (manufacture by Takara Bio) to obtain the expression vector pPTB-EX. The nucleotide sequence of the obtained plasmid was analyzed, and it was confirmed that the inverse PCR caused no mutations.

7-5) Construction of Vector pPTPCN for Recombinant PCN Expression

The PCN gene isolated by the method described in Example 3 was inserted into the XbaI site of expression vector pPTB-EX to construct vector pPTPCN for expressing recombinant PCN. To add the XbaI recognition sequence to the 5'- and 3'-termini of the coding region of the PCN gene, a PCR was carried out using pPCN as a template and the following primers (PCN-XbaIPtN and PCN-XbaIPtC) in which the XbaI recognition sequence was added to the 5'- and 3'-termini of the coding region of the PCN gene.

```
PCN-XbaIPtN:
                            (SEQ ID NO.: 19)
GGTCTAGAGGTCAAAATGCGAGGATTATACTCCCT

PCN-XbaIPtC:
                            (SEQ ID NO.: 20)
GGTCTAGACTACTCATCCACAGCGAATCGG
```

Figure 3:
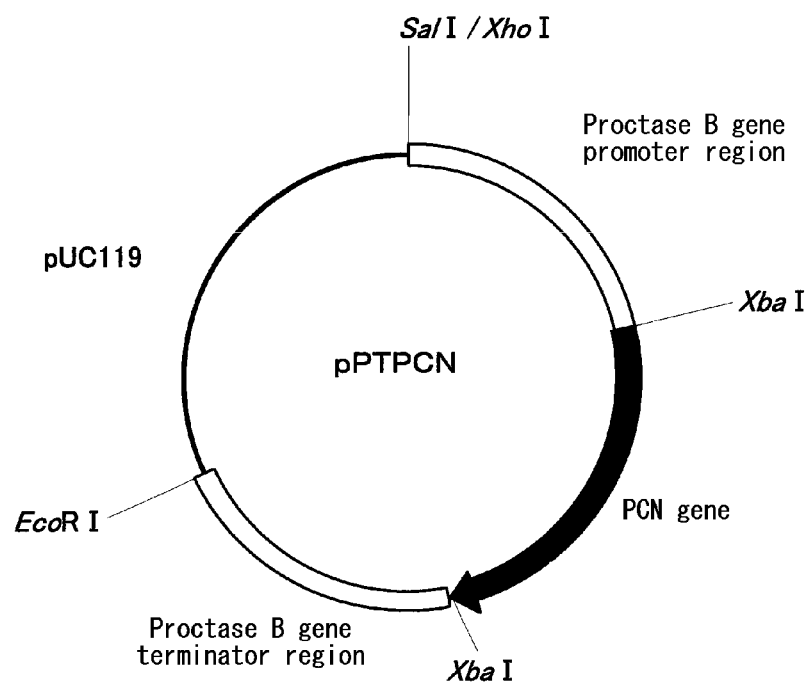
FIG. 3 is a restriction map of plasmid pPTPCN.

Primestar MAX DNA POLYMERASE (manufactured by Takara Bio) was used in the PCR, in which a cycle composed of a reaction at 98° C. for 10 seconds, a reaction at 55° C. for 5 seconds, and a reaction at 72° C. for 60 seconds was repeated 30 times. As a result, a DNA fragment of approximately 2.3 kb was amplified. The resulting PCR reaction liquid and a QIAQUICK PCR PURIFICATION KIT (manufactured by Qiagen) were used to purify the DNA fragment. The DNA fragment was dissolved in 50 μL of a TE buffer, and digested with restriction enzyme XbaI. The digested fragment was ligated using a ligation kit Ver. 2 (manufacture by Takara Bio) to pPTB-EX, which had been digested with XbaI and dephosphorylated, to obtain plasmid pPTPCN (SEQ ID NO.: 21, FIG. 3). The DNA sequence of the PCN gene inserted into the plasmid was analyzed, and it was confirmed that the PCR caused no mutations.

Example 8

Transformation of *Aspergillus niger* Var. *Macrosporus* with PCN-Expression Vector pPTPCN and Expression of Recombinant PCN A transformation of *Aspergillus niger* var. *macrosporus* with PCN-expression vector pPTPCN was carried out by transforming a niaD-deficient strain of *Aspergillus niger* var. *macrosporus* using a niaD gene as a selective marker gene.

8-1) Isolation of niaD-Deficient Strain Nia2

Spores of *Aspergillus niger* var. *macrosporus* were applied on a Czapek medium-N (0.1% $K_2HPO_4$, 0.05% $MgSO_4\cdot 7H_2O$, 0.05% KCl, 0.001% $FeSO_4\cdot 2H_2O$, 3% sucrose, 1.5% purified agar, pH5.5-6.0) supplemented with 0.188% Na-glutamate and 3% $KClO_3$, and incubated at 30° C. for 5 to 7 days. Colonies were replicated to each medium in which the nitrogen source of the Czapek medium was replaced with $NO_3$, $NH_4$, or Glutamate, and incubated at 30° C. for 5 to 7 days. Among the replicated colonies, a strain which could grow on the medium containing $NH_4$ or Glutamate as the nitrogen source, but could not grow on the medium containing $NO_3$ as the nitrogen source was isolated as a niaD-deficient strain Nia2.

8-2) Isolation of Selection Marker Gene, niaD Gene

A PCR using the following primers Nia-N and Nia-C, designed on the basis of the 5'- and 3'-termini of the coding region of a niaD gene of *Aspergillus niger* reported by Uncle et al. [Uncle, S. E., Cambell, E. I., Punt, P. J., Hawker, K. L., Contreras, R., Hawkins, A. R., Van Den Hondel, C. A. and Kinghorn, J. R., "The *Aspergillus niger* niaD gene encoding nitrate reductase:upstream nucleotide and amino acid sequence comparisons", Gene 111(2), 149-155(1992)], was carried out to amplify the coding region of a niaD gene of *Aspergillus niger* var. *macrosporus*.

```
Nia-N:
                                        (SEQ ID NO.: 22)
ATGGCGACTGTCACTGAGGTG

Nia-C:
                                        (SEQ ID NO.: 23)
TTAGAAGAAATGAAGGTCCGA
```

The PCR was carried out using genomic DNA of *Aspergillus niger* var. *macrosporus* and an LA PCR™ KIT Ver2.1 (manufactured by Takara Bio). In the PCR, after a reaction at 94° C. for 1 minute, a cycle composed of a reaction at 94° C. for 30 seconds, a reaction at 55° C. for 30 seconds, and a reaction at 72° C. for 3 minutes was repeated 30 times, and a reaction at 72° C. for 7 minutes was carried out. As a result, a DNA fragment of approximately 3 kb was amplified. The amplified DNA fragment was labeled using an ECL direct system (manufactured by Amersham Pharmacia Biotech) as a probe.

The coding region of the niaD gene prepared by the above method was used as a probe to isolate a clone containing the promoter and terminator regions of the niaD gene from the genomic DNA library, which was prepared by the method described in Example 7-1, of *Aspergillus niger* var. *macrosporus*. In a fashion substantially similar to that described in Example 7, the genomic DNA library was screened to obtain a positive clone. The obtained phage clone was analyzed by Southern blotting in a fashion substantially similar to that described in Example 7. As a result, an XbaI-digested fragment of approximately 6.5 kb showed common hybridization patterns to those of chromosomal DNA. This XbaI fragment was cloned into the XbaI recognition sequence site of pUC118 to obtain plasmid pPTnia118. The nucleotide sequence of the obtained plasmid was analyzed to determine the nucleotide sequence of 6416 bp (SEQ ID NO.: 24) containing the promoter and terminator regions of the niaD gene.

8-3) Introduction of PCN Gene into *Aspergillus niger* Var. *Macrosporus* Nia2 Strain The *Aspergillus niger* var. *macrosporus* Nia2 strain was cultivated in an S medium (3.0% glucose, 0.1% polypeptone, 1% yeast extract, 0.14% ammonium sulfate, 0.2% potassium phosphate, 0.03% magnesium sulfate, pH6.8) at 30° C. for 24 hours, and centrifuged at 3500 rpm for 10 minutes to collect the cells. The collected cells were washed with 0.5 mol/L sucrose, and suspended in an enzyme solution for preparing protoplasts (10 mg/mL β-glucuronidase, 3 mg/mL chitinase, 3 mg/mL zymolase, 0.5 mol/L sucrose), which had been filtrated through a 0.45 μm filter. The suspended mycelia was incubated at 30° C. for 60 minutes with shaking to prepare protoplasts. The suspension was filtrated through absorbent cotton, and centrifuged at 2500 rpm for 10 minutes to collect the protoplasts. The protoplasts were washed with an SUTC buffer (17.1% sucrose, 10 mmol/L Tris-HCl pH7.5, 10 mmol/L $CaCl_2$), and resuspended in 100 μL of the SUTC buffer. To the protoplast suspension, 7.5 μL of pPTPCN (1 μg/μL) and 2.5 μL of pPTnia118 (1 μg/μL) were added, and the mixture was allowed to stand on ice for 5 minutes. Further, 400 μL of a PEG solution (60% PEG4000, 10 mmol/L Tris-HCl pH7.5, 10 mmol/L $CaCl_2$) was added, and allowed to stand on ice for 20 minutes. After 10 mL of the SUTC buffer was further added, the whole was centrifuged at 2500 rpm for 10 minutes. The centrifuged protoplasts were suspended in 1 mL of the SUTC buffer, centrifuged at 4000 rpm for 5 minutes, and finally suspended in 100 μL of the SUTC buffer.

The resulting protoplasts were overlaid with soft agar on a modified Czapek medium (0.085% $NaNO_3$, 0.1% $K_2HPO_4$, 0.05% $MgSO_4\cdot 7H_2O$, 0.05% KCl, 0.001% $FeSO_4\cdot 2H_2O$, 17.1% sucrose, 1.5% purified agar, pH5.5-6.0), and incubated at 30° C. for 5 to 7 days. Colonies formed after the incubation was regarded as transformants.

8-4) PCN Expression and Measurement of Enzymatic Activity in Transformant of *Aspergillus niger* Var. *Macrosporus* Nia2 Strain The obtained transformants were cultivated in a P medium (1.0% starch, 6.0% soybean meal, 1.0% corn steep liquor, 0.3% ammonium sulfate, and 1% calcium carbonate) at 28° C. for 6 days. A supernatant of each culture was analyzed by SDS-PAGE to obtain a strain (No. 16) in which the band having a molecular weight of approximately 80 kDa, corresponding to the recombinant PCN, was observed. With respect to the culture supernatant of strain No. 16, and a supernatant obtained by similarly cultivating the Nia2 strain, the catalase activity was measured by the method described in Example 1. As shown in Table 1, the activity of strain No. 16 was 77 times or more that of the wild type, and it was confirmed that the recombinant PCN was expressed in strain No. 16.

TABLE 1

| | Catalase activity (u/mL) |
|---|---|
| Wild type | less than 300 u/mL |
| Strain No. 16 | 23300 u/mL |

In this regard, "1 unit" of the catalase activity was regarded as the amount of the enzyme capable of decomposing 1 μmol of hydrogen peroxide per minute. Further, the catalase activity of the culture supernatant of *Penicillium pinophilum* prepared by the method described in Example 1 was 385 U/mL. This result shows that the productivity of PCN remarkably increases by expressing PCN in *Aspergillus niger* var. *macrosporus* as a host.

8-5) Analysis of N-Terminal Amino Acid Sequence

The culture supernatant of the transformant No. 16 strain obtained in Example 8-4 was subjected to SDS-PAGE, and separated proteins were transferred to a PVDF membrane Immobilon-PSQ (manufactured by Millipore). The PVDF membrane was stained with Coomassie brilliant blue. A portion in which the protein of approximately 80 kDa was blotted was cut from the membrane, and subjected to an amino acid sequencer model 492 to determine the amino acid sequence of 11 residues at the amino-terminus. The amino sequence was as follows:

DDSNASSETEA (Amino acids 1-11 of SEQ ID NO.: 5)

This amino acid sequence was identical with the N-terminal amino acid of PCN derived from *Penicillium pinophilum*, and thus, it was confirmed that the protein of approximately 80 kDa was the recombinant PCN.

8-6) Evaluation of Thermostability in Recombinant PCN

As described in Example 1, the thermostability of naturally-occurring PCN produced by *Penicillium pinophilum* was 50%. The thermostability of the recombinant PCN obtained by the method described in Example 8-4 was evaluated by the method described in Example 1. As a result, the thermostability was 71.3%. This result revealed that the thermostability of the recombinant PCN was remarkably improved in comparison with that of naturally-occurring PCN.

Although the present invention has been described with reference to specific embodiments, various changes and modifications obvious to those skilled in the art are possible without departing from the scope of the appended claims.

Free Text in Sequence Listing

The nucleotide sequences of SEQ ID NOS.: 6-9 and 11-14 are artificially synthesized primer sequences, i.e., P catalase F (SEQ ID NO.: 6), P catalase R (SEQ ID NO.: 7), PCNF (SEQ ID NO.: 8), PCNR (SEQ ID NO.: 9), H catalase F (SEQ ID NO.: 11), H catalase R (SEQ ID NO.: 12), HCNF (SEQ ID NO.: 13), HCNR (SEQ ID NO.: 14), proctaseB-N(SEQ ID NO.: 15), proctaseB-C(SEQ ID NO.: 16), proctaseBNxba (SEQ ID NO.: 17), proctaseBCxba (SEQ ID NO.: 18), PCN-XbaIPtN (SEQ ID NO.: 19), PCN-XbaIPtC (SEQ ID NO.: 20), and Nia-N(SEQ ID NO.: 22), and Nia-C(SEQ ID NO.: 23), respectively.

The nucleotide sequence of ID NO.: 21 is plasmid pPT-PCN.

The abbreviations "N" at the 18th position of SEQ ID NO.: 6, the 3rd, 6th, and 12th positions of SEQ ID NO.: 11, and the 6th and 9th positions of SEQ ID NO.: 12 stand for an arbitrary nucleotide; and the abbreviation "N" at the 12th position of SEQ ID NO.: 12 stands for deoxyinosine.

The invention claimed is:

1. An isolated DNA encoding a protein selected from the group consisting of (1)-(5), wherein said DNA does not comprise a nucleotide sequence that is 100% identical to the nucleotide sequence of nucleotides 127-2403 of SEQ ID NO: 1:
   (1) a protein comprising the amino acid sequence of amino acids 1-692 of SEQ ID NO: 2;
   (2) a protein comprising an amino acid sequence in which one to 30 amino acids are deleted, substituted, and/or added relative to the amino acid sequence of amino acids 1-692 of SEQ ID NO: 2;
   (3) a protein comprising an amino acid sequence having 90% or more identity with the amino acid sequence of amino acids 1-692 of SEQ ID NO: 2;
   (4) a protein consisting of the amino acid sequence of amino acids 1-692 of SEQ ID NO: 2; and
   (5) the protein of (1)-(3), wherein said protein comprises, at the N-terminus, the amino acid sequence of amino acids −1 to −42 of SEQ ID NO: 2, or an amino acid sequence in which one to 10 amino acids are deleted, substituted, and/or added relative to the amino acid sequence of amino acids −1 to −42 of SEQ ID NO: 2.

2. An isolated DNA encoding a protein selected from the group consisting of (1)-(4), wherein said DNA does not comprise a nucleotide sequence that is 100% identical to the nucleotide sequence of nucleotides 97-2749 of SEQ ID NO: 3:
   (1) a protein comprising the amino acid sequence of amino acids 1-684 of SEQ ID NO: 4;
   (2) a protein comprising an amino acid sequence having 99% or more identity with the amino acid sequence of amino acids 1-684 of SEQ ID NO: 4;
   (3) a protein consisting of the amino acid sequence of amino acids 1-684 of SEQ ID NO: 4; and
   (4) the protein of (1) to (3), wherein said protein further comprises, at the N-terminus, the amino acid sequence of amino acids −1 to −32 of SEQ ID NO: 4, or an amino acid sequence in which one to 10 amino acids are deleted, substituted, and/or added relative to the amino acid sequence of amino acids −1 to −32 of SEQ ID NO: 4.

3. The DNA according to claim 1, wherein one or more introns are missing in said DNA relative to the nucleotide sequence of nucleotides 127-2403 of SEQ ID NO: 1.

4. The DNA according to claim 2, wherein one or more introns are missing in said DNA relative to the nucleotide sequence of nucleotides 97-2749 of SEQ ID NO: 3.

5. The DNA according to claim 4, wherein said one or more introns that are missing are introns selected from the group consisting of nucleotides 283-463, 667-747, 771-846, 1008-1160, 1218-1270, and 1842-1895 of SEQ ID NO: 3.

6. The DNA according to claim 3, wherein said one or more introns that are missing are introns selected from the group consisting of nucleotides 322-372, 599-651, 1068-1113, and 1279-1326, of SEQ ID NO: 1.

7. An expression vector comprising the DNA according to claim 1 or 6.

8. A host microorganism transformed with the DNA according to claim 1 or 6, or transformed with an expression vector comprising said DNA.

9. The host microorganism according to claim 8, wherein the host microorganism is a filamentous fungus.

10. The host microorganism according to claim 9, the filamentous fungus is a filamentous fungus belonging to genus *Aspergillus, Penicillium, Humicola, Trichoderma*, or *Acremonium*.

11. A process for producing a thermostable catalase, said process comprising cultivating the host microorganism according to claim 8, and collecting the thermostable catalase from the culture obtained by the cultivation.

12. An expression vector comprising the DNA according to claim 2 or 5.

13. A host microorganism transformed with the DNA according to claim 2 or 5, or transformed with an expression vector comprising said DNA.

14. The host microorganism according to claim 13, wherein the host microorganism is a filamentous fungus.

15. The host microorganism according to claim 14, the filamentous fungus is a filamentous fungus belonging to genus *Aspergillus, Penicillium, Humicola, Trichoderma*, or *Acremonium*.

16. A process for producing a thermostable catalase, said process comprising cultivating the host microorganism according to claim 13, and collecting the thermostable catalase from the culture obtained by the cultivation.

17. A host microorganism transformed with a DNA comprising the nucleotide sequence of nucleotides 127-2403 of SEQ ID NO: 1, or transformed with an expression vector comprising said DNA, wherein said host microorganism is a filamentous fungus belonging to a genus selected from the group consisting of *Aspergillus, Humicola, Trichoderma,* and *Acremonium.*

18. A host microorganism transformed with a DNA comprising the nucleotide sequence of nucleotides 97-2749 of SEQ ID NO: 3, or transformed with an expression vector comprising said DNA, wherein said host microorganism is a filamentous fungus belonging to a genus selected from the group consisting of *Aspergillus, Penicillium, Trichoderma,* and *Acremonium.*

19. A process for producing a thermostable catalase, said process comprising cultivating the host microorganism according to claim 17, and collecting the thermostable catalase from the culture obtained by the cultivation.

20. A process for producing a thermostable catalase, said process comprising cultivating the host microorganism according to claim 18, and collecting the thermostable catalase from the culture obtained by the cultivation.

* * * * *